United States Patent
Barbier et al.

[11] Patent Number: 6,043,385
[45] Date of Patent: Mar. 28, 2000

[54] VITAMIN D DERIVATIVES

[75] Inventors: Pierre Barbier, Rixheim, France; Franz Bauer, Reinach; Peter Mohr, Basel, both of Switzerland; Marc Muller, Saint-Louis, France; Wolfgang Pirson, Weil am Rhein, Germany

[73] Assignee: Hoffman-La Roche Inc., Nutley, N.J.

[21] Appl. No.: 09/203,088

[22] Filed: Dec. 1, 1998

[30] Foreign Application Priority Data

Dec. 16, 1997 [EP] European Pat. Off. ............. 97122123

[51] Int. Cl.$^7$ .................... C07C 401/00; A61N 45/00
[52] U.S. Cl. ............................................ 552/653; 514/167
[58] Field of Search ............................... 552/653; 514/167

[56] References Cited

U.S. PATENT DOCUMENTS

| | | | |
|---|---|---|---|
| 5,686,435 | 11/1997 | Hesse et al. | 514/167 |
| 5,756,733 | 5/1998 | Hesse et al. | 544/164 |
| 5,763,429 | 6/1998 | Bishop et al. | 552/653 |
| 5,786,347 | 7/1998 | Hesse et al. | 514/167 |
| 5,811,562 | 9/1998 | Hesse et al. | 552/653 |
| 5,840,938 | 11/1998 | DeLuca et al. | 552/653 |
| 5,856,536 | 1/1999 | DeLuca et al. | 552/653 |
| 5,880,114 | 3/1999 | DeLuca et al. | 552/653 |

FOREIGN PATENT DOCUMENTS

WO 94/26707  11/1994  WIPO.

OTHER PUBLICATIONS

Chem. Pharm. Bull. 45(1) pp. 185–188 (1997).
Chem. Pharm. Bull. 39(2) pp. 3221–3224 (1991).
Patent Abstracts of Japan, 1994, vol. 18, No. 385 (C–1227), JP 06107625.

*Primary Examiner*—Jose' G. Dees
*Assistant Examiner*—Sabiha N. Qazi
*Attorney, Agent, or Firm*—George W. Johnston; Patricia S. Rocha-Tramaloni; Robert A. Silverman

[57] ABSTRACT

The present invention relates to vitamin D derivatives of the formula I

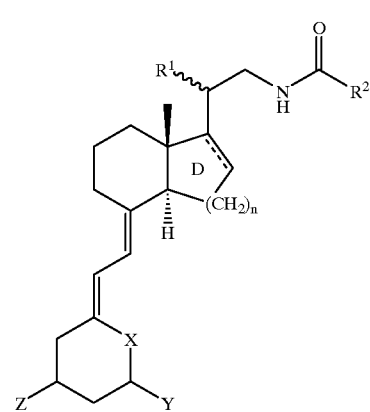

wherein
X is C=$CH_2$ or $CH_2$;
Y is hydrogen, fluorine or hydroxy
Z is hydroxy
n is 1 or 2
$R^1$ is lower alkyl,
$R^2$ is a branched alkyl having 3 to 8 carbon atoms which is unsubstituted or substituted with one or more halogen or OH substituents, or is a phenyl group which is unsubstituted or substituted with a branched alkyl having 3 to 8 carbon atoms which is unsubstituted or substituted with one or more halogen or OH substituents;
and the dotted carbon-carbon bond in ring D is —C—C— or —C=C—; or a pharmaceutically usable salt thereof.

37 Claims, No Drawings

VITAMIN D DERIVATIVES

SUMMARY OF THE INVENTION

The invention relates to a compound of the formula I

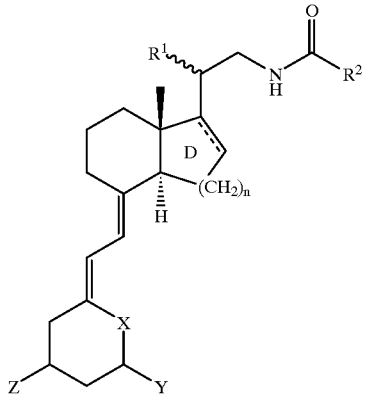

wherein

X is C=CH$_2$ or CH$_2$;

Y is hydrogen, fluorine or hydroxy

Z is hydroxy n is 1 or 2

R$^1$ is lower alkyl,

R$^2$ is a branched alkyl having 3 to 8 carbon atoms which is unsubstituted or substituted with one or more halogen or OH substituents, or is a phenyl group which is unsubstituted or substituted with a branched alkyl having 3 to 8 carbon atoms which is unsubstituted or substituted with one or more halogen or OH substituents;

and the dotted carbon-carbon bond in ring D is —C—C— or —C=C—; or a pharmaceutically usable salt thereof.

The compound of formula I are useful for treating vitamin D dependent disorders. Examples of such disorders are hyperproliferative skin diseases such as psoriasis, basal cell carcinomas, disorders of keratinization and keratosis; neoplastic diseases such as leukemia; disorders of the sebaceous glands such as acne and seborrhoic dermatitis; osteoporosis; hyperparathyroidism accompanying renal failure; and diseases which require modulation of the immune system, such as transplant rejection and graft vs. host disease.

DETAILED DESCRIPTION OF THE INVENTION

The invention relates to vitamin D derivatives of the formula I

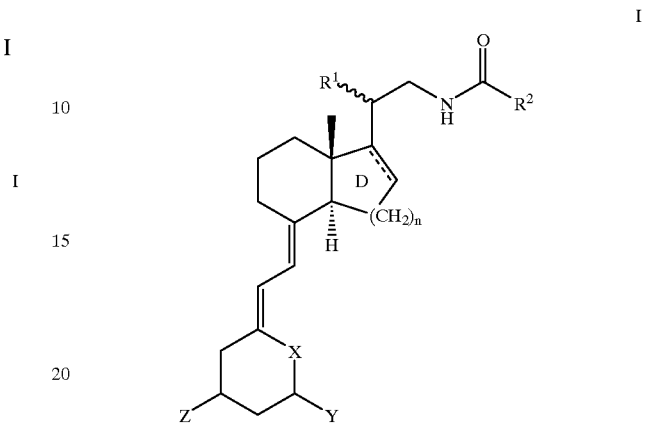

wherein

X is C=CH$_2$ or CH$_2$;

Y is hydrogen, fluorine or hydroxy

Z is hydroxy n is 1 or 2

R$^1$ is lower alkyl,

R$^2$ is a branched alkyl having 3 to 8 carbon atoms which is unsubstituted or substituted with one or more halogen or OH substituents, or is a phenyl group which is unsubstituted or substituted with a branched alkyl having 3 to 8 carbon atoms which is unsubstituted or substituted with one or more halogen or OH substituents;

and the dotted carbon-carbon bond in ring D is —C—C— or —C=C—; or a pharmaceutically usable salt thereof.

The present invention further relates to a process for the manufacture of compounds of formula I, to pharmaceutical compositions based on compounds of formula I or their salts, to the use of compounds of formula I for the treatment of vitamin D dependent disorders and for the manufacture of pharmaceutical compositions for the treatment of vitamin D dependent disorders.

The term "vitamin D dependent disorders" refers to disorders which can be treated or prevented by the administration of compounds having vitamin D activity, such as vitamin D$_3$ or derivatives, in particular hydroxylated derivatives thereof, e.g. calcitriol. Examples of such disorders are hyperproliferative skin diseases such as psoriasis, basal cell carcinomas, disorders of keratinization and keratosis; neoplastic diseases such as leukemia; disorders of the sebaceous glands such as acne and seborrhoic dermatitis; osteoporosis; hyperparathyroidism accompanying renal failure; and diseases which require modulation of the immune system, such as transplant rejection and graft vs. host disease.

The term "lower alkyl" as used herein denotes alkyl residues containing 1 to 5 carbon atoms, such as methyl, ethyl, isopropyl, isobutyl, tert.-butyl, pentyl, amyl and 3-pentyl.

The term "branched alkyl having 3 to 8 carbon atoms which is unsubstituted or substituted with one or more halogen or OH substituents" as used herein denotes alkyl residues containing 3 to 8 carbon atoms as i-propyl, tert. butyl, i-butyl, these groups being optionally substituted by halogen and/or hydroxy; such groups are e.g. 2-hydroxy-2-methylpropyl, 2-hydroxy-2-trifluoromethylpropyl and, 3,3,3-trifluoro-2-hydroxy-2-trifluoromethylpropyl.

The term "halogen" as used herein denotes fluorine, chlorine, bromine or iodine, preferred halogen substituents are fluorine.

The term "phenyl group which is unsubstituted or substituted with a branched alkyl having 3 to 8 carbon atoms which is unsubstituted or substituted with one or more halogen or OH substituents" as used herein denotes for example 3-(1-hydroxy-1-methylethyl)phenyl.

In the structural formulas presented herein a broken bond ⫶ denotes that the substituent is below the plane of the paper and a wedged bond ▼ denotes that the substituent is above the plane of the paper. A bond ⁀ denotes that the substituent may be either below or above the plane of the paper. Variables Y and Z may also be either below or above the plane of the paper.

Compounds of formula I wherein $R^2$ is a branched alkyl having 3 to 8 carbon atoms which is unsubstituted or substituted with one or more halogen or OH substituents are preferred. Especially preferred are compounds of formula I wherein $R^2$ is 2-hydroxy-2-methylpropyl, 2-hydroxy-2-trifluoromethylpropyl or 3,3,3-trifluoro-2-hydroxy-2-trifluoromethylpropyl.

A further preferred group of compounds of formula I are compounds wherein n is 1 and the dotted carbon-carbon in ring D is —C—C—.

Especially preferred compounds of formula I are:

(E)—(R)—N—[(1R,3R,20S)-1,3-Dihydroxy-17a,20a-dihomo-19-nor-9,10-seco-pregna-5,7-dien-21-yl]-4,4,4-trifluoro-3-hydroxy-3-methyl-butyramide (E)—(S)—N—[(1R,3R,20S)-1,3-Dihydroxy-17a,20a-dihomo-19-nor-9,10-seco-pregna-5,7-dien-21-yl] -4,4,4-trifluoro-3-hydroxy-3-methyl-butyramide (E)—N—[(1R,3R,20S)-1,3-Dihydroxy-17a,20a-dihomo-19-nor-9,10-seco-pregna-5,7-dien-21-yl]-4,4,4-trifluoro-3-trifluoromethyl-3-hydroxy-butyramide 1:1 Mixture of (5Z,7E)—(R)—and (S)—N—[(1S,3R,20S)-1,3-Dihydroxy-17a,20a-dihomo-9,10-seco-pregna-5,7,10(19),17-tetraen-21-yl]-4,4,4-trifluoro-3-hydroxy-3-methyl-butyramide 1:1 Mixture of (E)—(R)—and (S)—N—(1R,3R,20S)-1,3-Dihydroxy-17a,20a-dihomo-19-nor-9,10-seco-pregna-(5,7,17-trien-21-yl)-4,4,4-trifluoro-3-trifluoromethyl-3-hydroxy-butyramide 1:1 Mixture of —[(5E,7E)—(R)— and —(S)-4,4,4-trifluoro-3-hydroxy-N—[(1S,3R,20S)-1,3-dihydroxy-20-methyl-9,10-seco-pregna-5,7,10(19)-trien-21-yl]-3-methyl-butyramide 1:1 Mixture of (E)—(R)— and (S)—N—[(1R,3R,20S)-1,3-dihydroxy-20-methyl-19-nor-9,10-seco-pregna-5,7-dien-21-yl]-4,4,4-trifluoro-3-hydroxy-3-methyl-butyramide E—(R)—N—[(1R,3R,20S)-1,3-Dihydroxy-20-methyl-19-nor-9,10-seco-pregna-5,7-dien-21-yl]-4,4,4-trifluoro-3-hydroxy-3-methyl-butyramide (E)—(1R,3R,20S)—N-(1,3-Dihydroxy-20-methyl-19-nor-9,10-seco-pregna-5,7-dien-21-yl)-4,4,4-trifluoro-3-hydroxy-3-trifluoromethyl-butyramide (E)—(1R,3R,20S)—N-(1,3-Dihydroxy-20-methyl-19-nor-9,10-seco-pregna-5,7-dien-21-yl)-2-hydroxy-2-methyl-propionamide 1:1 Mixture of (5Z,7E)—(R)— and (S)-4,4,4-trifluoro-3-hydroxy-3-methyl-N—[(3S,20S)-3-hydroxy-20-methyl-9,10-seco-pregna-5,7,10(19)-trien-21-yl]-butyramide (E)—(S)—N—[(1R,3R,20S)-1,3-dihydroxy-20-methyl-19-nor-9,10-seco-pregna-5,7-dien-21-yl]-4,4,4-trifluoro-3-hydroxy-3-methyl-butyramide (E)—(R)—N—[(1R,3R,20S)-1,3-dihydroxy-20-methyl-19-nor-9,10-seco-pregna-5,7-dien-21-yl]-4,4,4-trifluoro-3-hydroxy-3-methyl-butyramide 1:1 Mixture of —[(5Z,7E)—(R)— and (S)—N—[(1S,3R,20S)-1,3-dihydroxy-20-methyl-9,10-seco-pregna-5,7,10(19)-trien-21-yl]-4,4,4-trifluoro-3-hydroxy-3-methyl-butyramide 1:1 Mixture of (E)—(R)— and (S)—N—[(1R,3R,20R)-1,3-dihydroxy-20-methyl-19-nor-9,10-seco-pregna-5,7-dien-21-yl]-4,4,4-trifluoro-3-hydroxy-3-methyl-butyramide In accordance with the invention the compounds of formula I wherein the dotted carbon-carbon bond in ring D is —C—C— can be prepared according to a process as depicted in Schemes 1 or 2

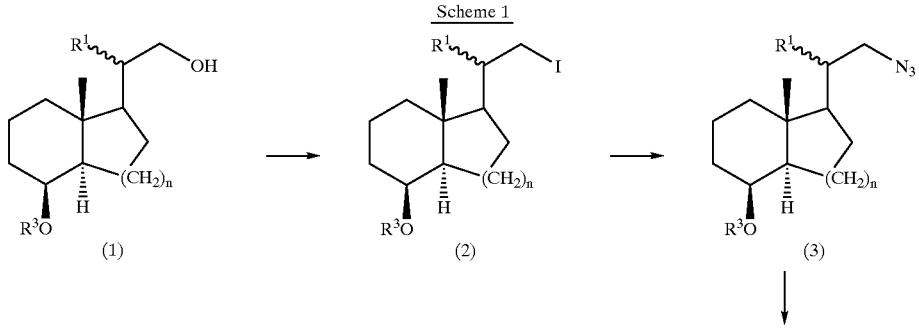

Scheme 1

-continued

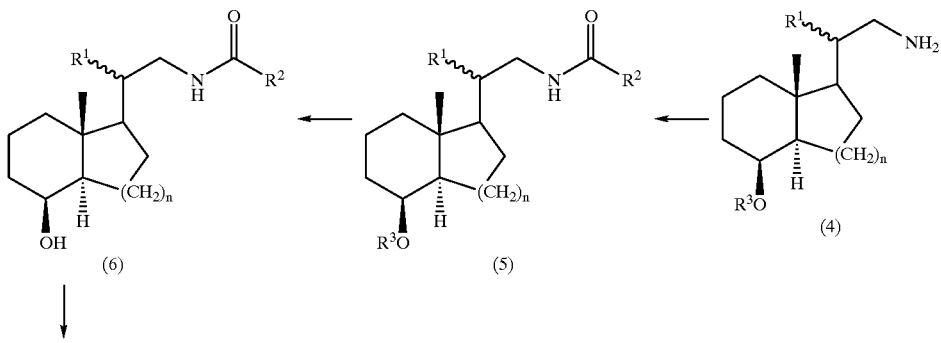

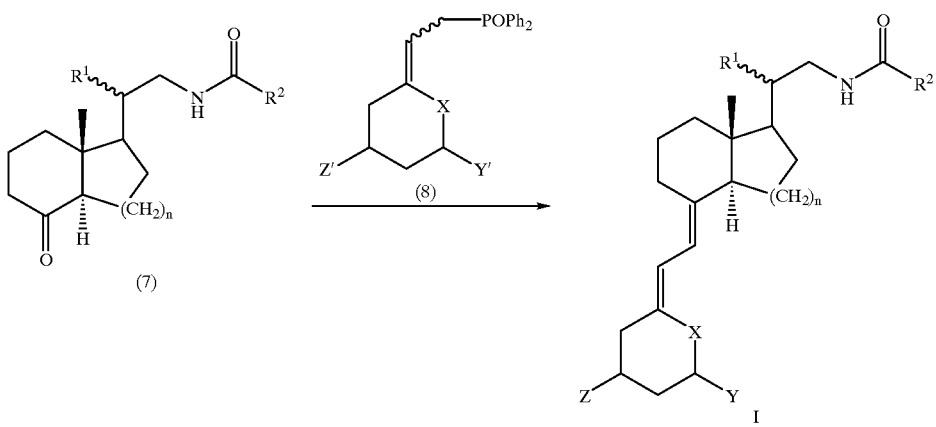

wherein $R^1$, $R^2$, X, Y and Z have the definitions given above, $R^3$ is a hydroxy protecting group and Y' is hydrogen, fluorine or protected hydroxy and Z' is protected hydroxy.

According to Scheme 1 a [(2-halo-1-alkyl-ethyl)-4a-methyl-decahydro-naphthalen-1-yloxy]-derivative (or a 4[(2-halo-1-alkyl-ethyl)-7a-methyl-octahydro-inden-4-yloxy]-derivative, if appropriate) (2) is prepared by halogenation of the corresponding primary alcohol (1), The primary alcohol (1) is obtained according to known methods, such as described in EP A 0 771 789. The compound (2) is then reacted with sodium azide in a polar solvent e.g. dimethylsulfoxide or N,N-dimethylformamide to form the azide (3). Subsequent reduction of the azido group and reaction of the amine (4) with an acid of formula $HOOCR^2$ yields the corresponding amides (5). The hydroxy group in the C—ring is deprotected and oxidized to yield keto intermediate (7).

The reaction of a compound (7) with a compound of the formula (8) can be carried out under the conventional conditions of a Wittig reaction, after optional protection of a hydroxy group present in $R^2$, i.e. by means of a base, e.g., butyl lithium, in an inert organic solvent, such as tetrahydrofuran. The compounds of formula I are obtained by cleaving the hydroxy protecting groups.

The hydroxy protecting group $R^3$ can be any conventional hydroxy protecting group. Examples of such groups are silyl ether protecting groups such as tert.-butyl-dimethylsilanyl or tert.-butyl-diphenylsilanyl. Another example of a hydroxy protecting group is tetrahydropyranyl. The removal of the hydroxy protecting groups R3 can be effected in a manner known per se for the removal of such groups. For instance, silylether can be removed by treatment with fluoride reagents, such as hydrogen fluoride or tetrabutyl ammonium fluoride in tetrahydrofuran.

The cyclohexylidene-ethyl-diphenyl-phosphine oxide (8) can be prepared according to the method described in EP-A 97106547.9, see Scheme 3.

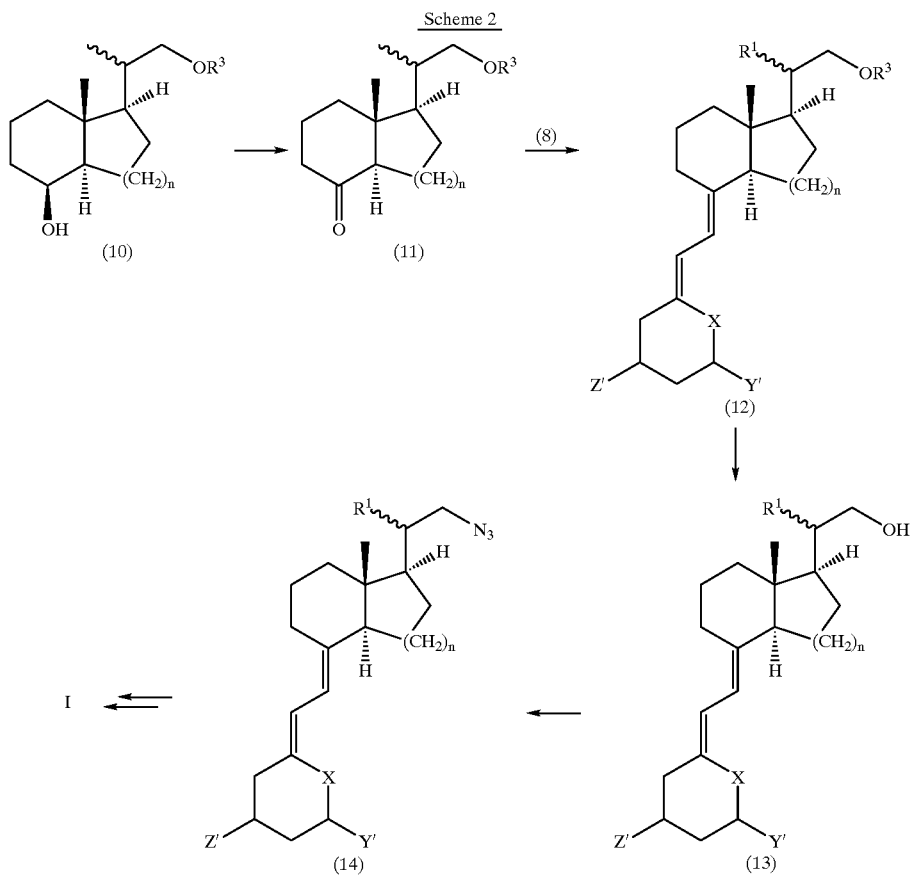

The compound (10) is known or obtained according to known methods, such as described in EP 771789.

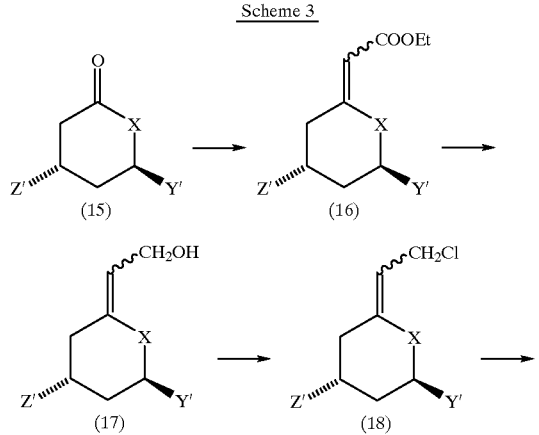

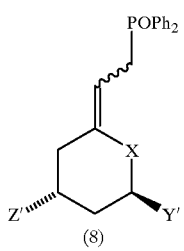

According to Scheme 3, the ketone (15), a known compound, is converted by a Peterson reaction into the ester (16) from which the alcohol (17) is obtained by reduction. Reaction of (17) with N-chlorosuccinimide in the presence of dimethylsulphide gives the chloride (18). Reaction of (18) with diphenyl-phosphine-lithium and work-up with 5% $H_2O_2$ in ethyl acetate gives the phosphinoxide (8).

The compounds of formula I wherein the dotted carbon-carbon bond of ring D is —C≡C— can be prepared according to a process as depicted in Scheme 4

Scheme 4

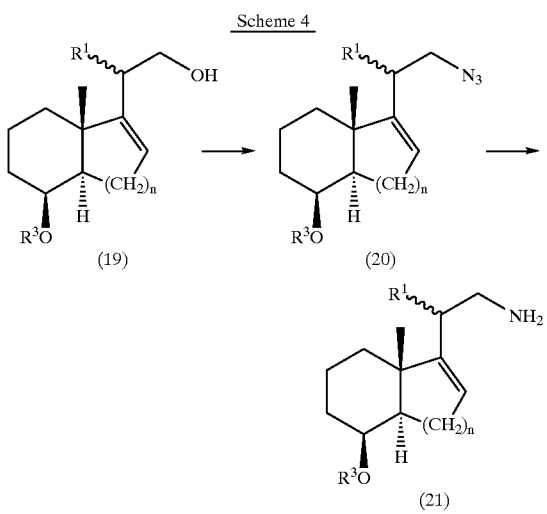

The hydroxyderivative (19), prepared according to the method described in EP-A 96116735, is converted by a Mitsunobo reaction using diisopropyl azodicarboxylate/ triphenylphosphine to the azido derivative (20). The azido group is reduced to the corresponding amine which is then converted into the amide (21) according to the method described in Scheme 1.

The compounds of formula I as described above can be administered orally or topically, preferably orally, for the treatment of hyperproliferative skin diseases such as psoriasis, basal cell carcinomas, disorders of keratinization, and keratosis, or for the treatment of neoplastic diseases such as leukemia, or for the treatment of osteoporosis and hyperparathyroidism, to warmblooded animals which need such treatment. More specifically, the compounds of formula I as described above can be administered orally to an adult human in dosages that are in the range of about 0.5 to 1000 μg per day, or can be administered topically in dosages that are in the range of about 0.5 to 1000 μg per gram of topical formulation per day, for the treatment of the above diseases.

The dosage of the compounds of formula I can vary within wide limits depending on the illness to be treated, the age and the individual condition of the patient and on the mode of administration and will, of course, be fitted to the individual requirements in each particular case.

Oral dosage forms comprising compounds of formula I of the invention may be incorporated in capsules, tablets and the like with pharmaceutically acceptable carrier materials. Illustrative of such carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, absorbable, water-soluble and emulsion-type bases such as petrolatum, lanolin, polyethylene glycols and the like. Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like. Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecoamine.

As used herein, the term "topical" denotes the use of the active ingredient, incorporated in a suitable pharmaceutical carrier, and applied at the site of the disorder for the exertion of local action. Accordingly, the topical composition includes those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials.

The pharmacological properties of the compounds of the formula I can be determined by the following test procedures:

1. Calcium liability (tolerance test in mice):

This test gives a global picture of calcemic liability. Profound changes in calcium homeostasis strongly affect the weight development of the animals. This parameter was used as a primary test for tolerance. Mice (25–30 g body weight) received daily subcutaneous administrations of the vitamin D derivative for 4 consecutive days. Body weight was registered just before and at the end of a 5 day treatment period. The "highest tolerated dose" ($HTD_{sc}$) in mice is the dose which results in zero weight gain during this treatment period.

For calcitriol a HTD of 0.5 μg/kg was observed. In comparison thereto, for the compounds of formula I specifically named as products in the above Examples, HTD figures ranging from 1 to 5 μg/kg for the four less tolerated compounds, up to 400 μg/kg for the four best tolerated compounds were observed.

2. Vitamin D receptor activation (VDR)

In order to measure the activation of the vitamin D receptor (VDR) by vitamin D analogs in cells a transcription activation assay was used. COS cells were cotransfected with the human VDR (expressed in pSG5) and a reporter gene containing three response elements (VDRE3) from the rat osteocalcine gene, the thymidine kinase basal promoter, and the luciferase reporter gene, respectively.

The following compounds were tested with respect to VDR activation:

A: (E)—(1R,3R,20S)—N-(1,3-Dihydroxy-20-methyl-19-nor-9,10-seco-pregna-5,7-dien-21-yl)-4,4,4-trifluoro-3-hydroxy-3-trifluoromethyl-butyramide B: 1:1 Mixture of (E)—(R)— and (S)—N—[(1R,3R,20S)-1,3-dihydroxy-20-methyl-19-nor-9,10-seco-pregna-5,7-dien-21-yl]-4,4,4-trifluoro-3-hydroxy-20-methyl-butyramide C: (E)—(1R,3R,20S)—N-(1,3-Dihydroxy-20-methyl-19-nor-9,10-seco-pregna-5,7-dien-21-yl)-2-hydroxy-2-methyl-propionamide D: 1:1 Mixture of [(5Z,7E)—(R)— and (S)—N—[(1S,3R,20S)-1,3-dihydroxy-20-methyl -9,10-seco-pregna-5,7,10(19)-trien-21-yl]-4,4,4-trifluoro-3-hydroxy-3-methyl-butyramide E: 1:1 Mixture of (E)—(R)— and (S)—N—[(1R,3R,20R)-1,3-dihydroxy-20-methyl-19-nor-9,10-seco-pregna-5,7-dien-21-yl]-4,4,4-trifluoro-3-hydroxy-3-methyl-butyramide F: (E)—(R)—N—[(1R,3R,20S)-1,3-Dihydroxy-17a,20a-dihomo-19-nor-9,10-seco-pregna-5,7-dien-21-yl]-4,4,4-trifluoro-3-hydroxy-3-methyl-butyramide G: (E)—(S)—N—[(1R,3R,20S)-1,3-Dihydroxy-17a,20a-dihomo-19-nor-9,10-seco-pregna-5,7-dien-21-yl]-4,4,4-trifluoro-3-hydroxy-3-methyl-butyramide H: (E)—N—[(1R,3R,20S)-1,3-Dihydroxy-17a,20a-dihomo-19-nor-9,10-seco-pregna-5,7-dien-21-yl]-4,4,4-trifluoro-3-trifluoromethyl-3-hydroxy-butyramide I: 1:1 Mixture of —[(5E,7E)—(R)— and —(S)-4,4,4-trifluoro-3-hydroxy-N—[(1S,3R,20S)-1,3-dihydroxy-20-methyl-9,10-seco-pregna-5,7,10(19)-trien-21-yl]-3-methyl-butyramide J: E—(R)—N—[(1R,3R,20S)-1,3-Dihydroxy-20-methyl-19-nor-9,10-seco-pregna-5,7-dien-21-yl]-4,4,4-trifluoro-3-hydroxy-3-methyl-butyramide The table shows that the tested compounds are quite potent with respect to VDR activation. Moreover all of them have a greater therapeutic window than calcitriol ( as indicated by the TI shift* vs calcitriol).

| compound | VDR act. ($ED_{50}$, nanomolar) | HTD sc, mouse µg/kg | HTD/VDR | TI shift* |
|---|---|---|---|---|
| Calcitriol | 2.6 | 0.5 | 0.19 | 1 |
| A | 0.47 | 3 | 6.4 | 34 |
| B | 1.7 | 45 | 26.5 | 139 |
| C | 6.4 | 400 | 62.5 | 329 |
| D | 1.6 | 10 | 6.3 | 33 |
| E | 0.35 | 1 | 2.9 | 15 |
| F | 0.6 | 5 | 8.3 | 44 |
| G | 0.18 | 4.5 | 25 | 132 |
| H | 0.5 | 2.3 | 4.6 | 24 |
| I | 40 | 130 | 3.3 | 17 |
| J | 2.1 | 22 | 10.5 | 55 |

HTDsc: highest tolerated subcutaneous dose (µg/kg) without weight loss
TI shift: shift in "therapeutic index", defined as the ratio HTD/VDR of the test compound divided by the ratio HTD/VDR of calcitriol. These compounds show biological effects at tolerated doses.

3. The mouse model

Epidermal thickening (acanthosis) in hairless mice is considered as indicative for an antipsoriatic potential. Analogues were tested for 4 days at different dosages in order to detect compounds which show this epidermal effect at subtoxic and non-toxic doses (dosage leading to slight or no weight loss). At the higest tolerated dose calcitriol itself was not able to elicit skin effects. The calcitriol data were obtained from animals treated for three days.

Hairless mice (Moro hr/hr) received daily administrations of the test compound in arachis oil by gavage for 4 days, using 2–5 different dosages (3 fold increments; 2 animals per dosage group). The mice were sacrificed at day 5 and skin biopsies were taken, fixed in formalin and treated for histological evaluation. Daily measurements of body weight allowed to judge toxicity (calcemic liability) and determine the non-toxic dose level defined as the dose which is tolerated without weight loss.

The results in the table below show that compound B, is far superior to calcitriol due to a better ratio between the effective dose and the maximal tolerated dose ($HTD_{po}$). This translates in a better separation between wanted skin effects ($ED_{50}$) and toxic calcemic effects.

| compound | $ED_{50}$ | $HTD_{po}$ | ratio (TI) $HTD/ED_{50}$ | TI shift |
|---|---|---|---|---|
| calcitriol | 500 | 1 | 0.002 | 1 |
| compound B | 80 | 20 | 0.25 | 125 |
| compound J | 50 | 8 | 0.16 | 80 |

$ED_{50}$: dose (µg/kg) causing half-maximal epidermal thickening
$HTD_{po}$: highest tolerated oral dose (µg/kg) without weight loss
TI shift: shift in "therapeutic index", is defined as ratio $HTD/ED_{50}$ for the test compound divided by the ratio $HTD/ED_{50}$ for calcitriol 4. The pig model Epidermal proliferation in minipigs is considered as indicative for an antipsoriatic potential. Compounds were tested for seven days at different doses in order to detect those which showed a skin effect at non calcemic dose (no calcemic effect). The pigs were daily observed as to adverse effects such as behavior, mobility, stool. At day seven bromodeoxyuridine (4 mg/kg) was injected intravenously into the treated pigs and 2 hours later skin biopsies (6 mm diameter) and blood were taken for analysis. The skin biopsies were fixed in formalin, and paraffin sections were prepared using standard procedures. Using standard immuno-histochemical techniques, cells in the S-phase (DNA synthesis phase) were labelled by the binding of a specific monoclonal antibody against the thymidine analogue bromodeoxyuridine. The number of labelled epidermal cells per unit of length along the surface was taken as a measure of epidermal proliferative activity (labelings index LI). Clinical chemistry was performed using Cobas Mira. Calcitriol itself did not induce hyperproliferation even at highly toxic does (9 times the dose that induces hypercalcemia).

| compound | Effective dose *µg/kg | Calcemic dose, µg/kg | TI (ratio Calc./Eff. | rel. shift |
|---|---|---|---|---|
| calcitriol | >22.5 | 3 | <0.15 | 1 |
| compound B | 0.5 | 5 | 10 | >67 |
| compound J | 0.17 | 5 | 29 | >196 |

*The effective dose is the dose that increases the normal LI at least 50%

No adverse effects were noted at the effective dose.

The following pharmaceutical compositions can be prepared in a known manner:

EXAMPLE A

| Soft Gelatine Capsule | mg/Capsule |
|---|---|
| Active Ingredient | 0.0001–1 |
| Butylated Hydroxytoluene (BHT) | 0.016 |
| Butylated Hydroxyanisole (BHA) | 0.016 |
| Fractionated Coconut Oil (Neobee M-5) or Miglyol 812 q.s | 160.0 |

EXAMPLE B

| Soft Gelatine Capsule | mg/Capsule |
|---|---|
| Active Ingredient | 0.0001–1 |
| α-Tocopherol | 0.016 |
| Miglyol 812 | q.s. |

EXAMPLE C

| Topical Cream | mg/g |
|---|---|
| Active Ingredient | 0.005–1 |
| Cetyl Alcohol | 1.5 |
| Stearyl Alcohol | 2.5 |
| Span 60 (Sorbitan monostearate) | 2.0 |
| Arlacel 165 (Glyceryl monostearate and polyoxyethylene glycol stearate blend) | 4.0 |
| Tween 60 (polysorbate 60) | 1.0 |
| Mineral Oil | 4.0 |
| Propylene Glycol | 5.0 |
| Propylparaben | 0.05 |
| BHA | 0.05 |
| Sorbitol Solution | 2.0 |
| Edetate Disodium | 0.01 |
| Methylparaben | 0.18 |
| Distilled Water | q.s. |

EXAMPLE D

| Topical ointment | mg/g |
|---|---|
| Active Ingredient | 0.005–1 |
| Propylenglycol | exc. ad ung. pro 1 g |

EXAMPLE 1

1.1. Preparation of (E)—(R)—N—[(1R,3R,20S)-1,3-Dihydroxy-17a,20a-dihomo-19-nor-9,10-seco-pregna-5,7-dien-21-yl]-4,4,4-trifluoro-3-hydroxy-3-methyl-butyramide a] (1S,4aR,5R,8aR)-[5-((S)-2-Azido-1-methyl-ethyl)-4a-methyl-decahydro-naphthalen-1-yloxy]-tert-butyl-dimethyl-silane

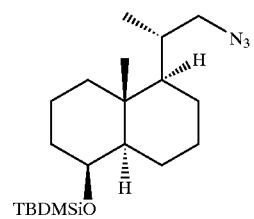

wherein TBDMSi is tert.-butyldimethylsilyl 3.61 g (8.01 mmol) of (1S,4aR,5R,8aR)-tert-Butyl-[5-[(S)-2-iodo-1-methyl-ethyl]-4a-methyl-decahydro-naphthalen-1-yloxy]-dimethyl-silane (preparation described in EP-A 96116735) was dissolved in 16 ml of abs. N,N-dimethylformamide and treated with 1.56 g (3 eq.) of $NaN_3$. The mixture was kept for 4.5 h at 60° and the progress of the reaction monitored by thin layer chromatography. Cooling to room temperature, pouring onto crushed ice, twofold extraction with hexane, washing with $NaHCO_3$ and drying over sodium sulfate left 2.87 g of a crude product, which was pure according to 250 MHz NMR and used as such for the next step.

MS: $(M)^+$ 365, $(M-t-butyl)^+$ 308.

b] (S)-2-[(1R,4aR,5S,8aR)-5-(tert-Butyl-dimethyl-silanyloxy)-8a-methyl-decahydro-naphthalen-1-yl]-propylamine

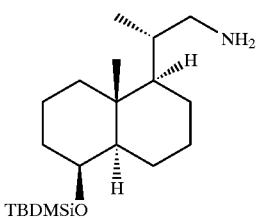

2.87 g of (1S,4aR,5R,8aR[5-((S)-2-Azido-1-methyl-ethyl)-4a-methyl-decahydro-naphthalen-1-yloxy]-tert-butyl-dimethyl-silane was dissolved in 75 ml of AcOEt and hydrogenated over 3.6 g of 10% Pd/C, which was added in three portions, during 8 h at ambient temperature and 1 atm of $H_2$. After filtration over a pad of Celite the solvents were removed. Flash chromatography ($SiO_2$, $AcOEt/NEt_3$=95/5) produced 1.543 g of the title compound as slightly brown oil.

MS: $(M+H)^+$ 340, $(M-t-butyl)^+$ 282.

c] 1:1 Mixture of (R)—and (S)—N—{(S)-2-[(1R,4aR,5S,8aR)-5-(tert-Butyl-dimethyl-silanyloxy)-8a-methyl-decahydro-naphthalen-1-yl]-propyl}-4,4,4-trifluoro-3-hydroxy-3-methyl-butyramide

15

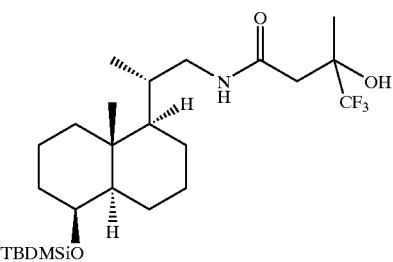

701 mg (2.06 mmol) of (S)-2-[(1R,4aR,5S,8aR)-5-(tert-Butyl-dimethyl-silanyloxy)-8a-methyl-decahydro-naphthalen-1-yl]-propylamine, 532 mg (1.5 eq.) of rac-3-trifluoromethyl-3-hydroxy-butyric acid, and 50 mg (0.2 eq.) of DMAP (N,N-dimethylaminopyridine) were dissolved in 20 ml of $CH_2Cl_2$. At 0° 680 mg (1.6 eq.) of DCC (dicyclohexylcarbodiimide) was added and the mixture allowed to react for 4 h at ambient temperature. The precipitated urea was filtered off and the filtrate evaporated to dryness. Flash chromatography ($SiO_2$, hexane/AcOEt=85/15) yielded in the less polar fractions 149 mg of unwanted 4,4,4-trifluoro-3-methyl-but-2-enoic acid {2-[5-(tert-butyl-dimethyl-silanyloxy)-8a-methyl-decahydro-naphthalen-1-yl]-propyl}-amide and in the more polar ones 811 mg of the title compound as colorless oil. Medium pressure chromatography of the latter ($SiO_2$, hexane/AcOEt=90/10) gave in the less polar fractions 367 mg of the (R)-butyramide and in the more polar ones 314 mg of the (S)-isomer, both as white foam. For determination of abs. configuration see d] below.

MS: $(M+H)^+$ 494, $(M-t-butyl)^+$ 436.

d] (R)-4,4,4-Trifluoro-3-hydroxy-N-[(S)-2-((1R,4aR,5S,8aR)-5-hydroxy-8a-methyl-decahydro-naphthalen-1-yl)-propyl]-3-methyl-butyramide

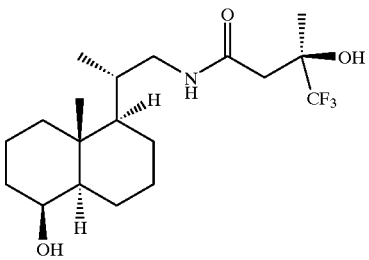

1.88 g of $nBu_4NF·3H_2O$ was carefully dried by stirring during 2 h at room temperature over 1.8 g of 3Å MS (molecular sieve). This solution was then added to 365 mg (0.739 mmol) of (R)—N—{(S)-2-[(1R,4aR,5S,8aR)-5-(tert-butyl-dimethyl-silanyloxy)-8a-methyl-decahydro-naphthalen-1-yl]-propyl}-4,4,4-trifluoro-3-hydroxy-3-methyl-butyramide and the mixture kept for 4 days at 50° thin layer chromatography indicated that still some starting material was left. Usual work-up provided a crude product which was treated once more in an analogous manner (1.88 g of dried $nBu_4NF·3H_2O$, 2 days, 50°). The reaction mixture was then poured onto crushed ice, extracted twice with ether, washed with water, dried over sodium sulfate, and the solvents carefully removed. Flash chromatography ($SiO_2$, hexane/AcOEt=7/3) afforded 237 mg of the title compound as white crystals. 20 mg thereof was recrystallized from hexane/trace amounts of AcOEt to give an analytically pure sample of mp. 133–134°, whose structure was secured by X-ray analysis.

e] (R)-4,4,4-Trifluoro-3-hydroxy-3-methyl-N-[(S)-2-((1R,4aR,8aR)-8a-methyl-5-oxo-decahydro-naphthalen-1-yl)-propyl]-butyramide

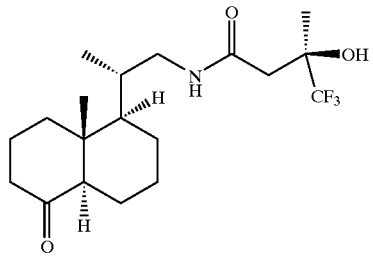

201 mg (0.532 mmol) of (R)-4,4,4-Trifluoro-3-hydroxy-N—[(S)-2-((1R,4aR,5S,8aR)-5-hydroxy-8a-methyl-decahydro-naphthalen-1-yl)-propyl]-3-methyl-butyramide was dissolved in 9 ml of abs. $CH_2Cl_2$ and reacted with 600 \mg (3 eq.) of PDC (pyridinium-dichromate). After stirring for 2.5 h the mixture was filtered over a pad of Celite and the solvent removed. Flash chromatography ($SiO_2$, hexane/AcOEt=7/3) yielded 189 mg of the title compound as white foam.

MS: $(M)^+$ 377, $(M-Me)^+$ 362, $(M-Me-CF_3)^+$ 308.

f] (R)-4,4,4-Trifluoro-3-hydroxy-N-[(S)-2-((1R,4aR,8aR)-8a-methyl-5-oxo-decahydro-naphthalen-1-yl)-propyl]-3-trimethylsilanyloxy-butyramide

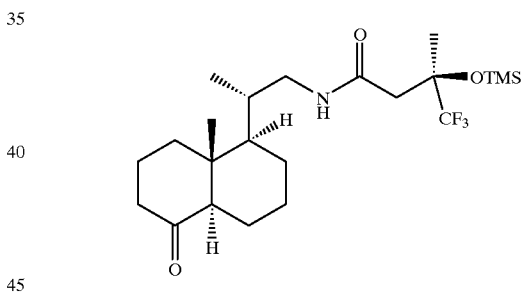

wherein TMS signifies trimethylsilyl 188 mg (0.498 mmol) of (R)-4,4,4-Trifluoro-3-hydroxy-3-methyl-N-[(S)-2-((1R,4aR,8aR)-8a-methyl-5-oxo-decahydro-naphthalen-1-yl)-propyl]-butyramide in 7 ml of abs. $CH_2Cl_2$ was treated with 0.438 ml (6 eq.) of TMS-imidazole and kept at room temperature over night. A second portion of 0.438 ml of TMS-imidazole was added and the reaction allowed to proceed for two days. Pouring onto crushed ice, extraction with ether, washing with water, and drying over sodium sulfate left a crude product, which was purified by flash chromatography ($SiO_2$, hexane/AcOEt=8/2). Thereby, 212 mg of the title compound was obtained as white foam.

CI-MS: $(M+H)^+$ 450, $(M+Na)^+$ 472.

g] (E)—(R)—N—[(S)-2-((1R,4aS,8aR)-5-{2-[(3R,5R)-3,5-Bis-(tert-butyl-dimethyl-silanyloxy)-cyclohexylidene]-ethylidene}-8a-methyl-decahydro-naphthalen-1-yl)-propyl]-4,4,4-trifluoro-3-methyl-3-trimethylsilanyloxy-butyramide

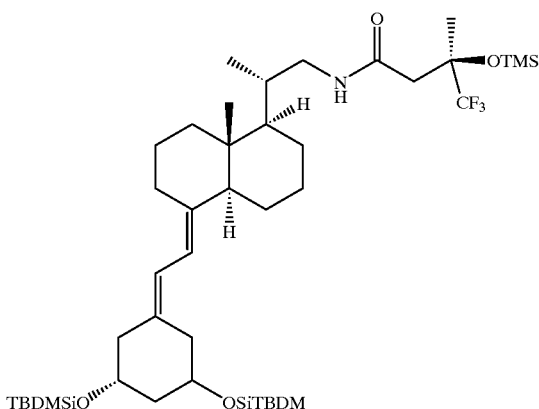

388 mg of carefully dried (3R,5R)-[2-[3,5-bis-(t-butyldimethyl-silanyloxy)-cyclohexylidene]-ethyl]-diphenyl-phosphine oxide (*Tetrahedron Lett.* 32, 7663 (1991)) was dissolved in 6.7 ml of abs. THF (tetrahydrofurane) and treated at −78° with 0.51 ml of nBuLi (1.5M, hexane). 15 Minutes later, 150 mg (0.334 mmol) of (R)-4,4,4-trifluoro-3-hydroxy-N—[(S)-2-((1R,4aR,8aR)-8a-methyl-5-oxo-decahydro-naphthalen-1-yl)-propyl]-3-trimethylsilanyloxy-butyramide, dissolved in 1.5 ml of abs. THF, was added to the deep red solution. The mixture was kept for 0.25 h at −78° and for 1 h at 0°. The discolored reaction mixture was then poured onto crushed ice, extracted twice with ether, washed with water, dried over sodium sulfate, and the solvents carefully removed. Flash chromatography (SiO$_2$, hexane/AcOEt=9/1) afforded 39 mg of the title compound as colorless oil, besides 100 mg of recovered ketone in the more polar fractions.

h] (E)—(R)—N—[(1R,3R,20S)-1,3-Dihydroxy-17a,20a-dihomo-19-nor-9,10-seco-pregna-5,7-dien-21-yl]-4,4,4-trifluoro-3-hydroxy-3-methyl-butyramide

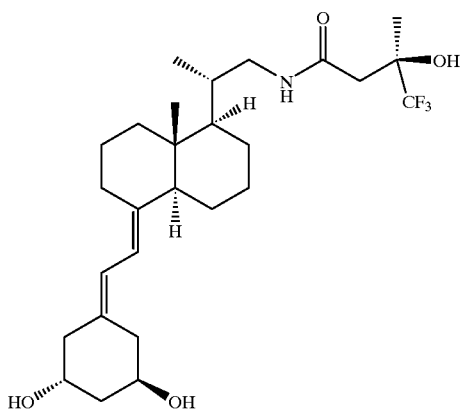

39 mg (0.0486 mmol) of (E)—(R)—N—[(S)-2-((1R,4aS,8a)-5-{2-[(3R,5R)-3,5-Bis-(tert-butyl-dimethyl-silanyloxy)-cyclohexylidene]-ethylidene}-8a-methyl-decahydro-naphthalen-1-yl)-propyl]-4,4,4-trifluoro-3-methyl-3-trimethylsilanyloxy-butyramide was treated with 8 equivalents of carefully dried TBAF (tetrabutylammoniumfluoride) (0.2M in THF) at 40° for 2 h. The reaction mixture was poured onto crushed ice, extracted twice with AcOEt, washed with water, dried over sodium sulfate and evaporated to dryness. Flash chromatography (SiO$_2$, AcOEt) yielded 38 mg of the title compound as white foam, contaminated with some TBDMS-OH.

MS: (M)$^+$ 501;

NMR (1H, DMSO, δ, TMS): 0.74 (s, 3H), 0.83 (d, 3H), 1.33 (s, 3H), 1.0–2.7 (m, 22H), 2.77 (m, 2H), 3.20 (m, 1H), 3.79 (m, 1H), 3.87 (m, 1H), 4.37 (d, OH), 4.48 (d, OH), 5.78 (d, 1H), 6.06 (d, 1H), 6.36 (s, OH), 8.03 (br t, NH).

EXAMPLE 1.2

In analogy to example 1.1, but using in step d] the (S)-butyramide, was obtained as colorless gum (E)—(S)—N—[(1R,3R,20S)-1,3-Dihydroxy-17a,20a-dihomo-19-nor-9,10-seco-pregna-5,7-dien-21-yl]-4,4,4-trifluoro-3-hydroxy-3-methyl-butyramide

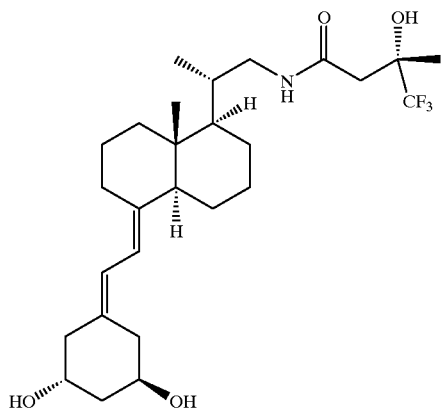

MS: (M)$^+$ 501;

NMR: (1H, CDCl$_3$, δ, TMS): 0.78 (s, 3H), 0.95 (d, 3H), 1.39 (s, 3H), 1.0–2.55 (m, 23H), 2.70–2.90 (m, 3H), 3.49 (m, 1H), 4.03 (m, 1H), 4.12 (m, 1H), 5.61 (br t, NH), 5.83 (d, 1H), 6.10 (br s, OH), 6.30 (d, 1H).

EXAMPLE 1.3

In analogy to example 1.1., but using in step c] 4,4,4-trifluoro-3-hydroxy-3-trifluoromethyl-butyric acid as coupling partner was obtained as colorless gum (E)—N-[(1R,3R,20S)-1,3-Dihydroxy-17a,20a-dihomo-19-nor-9,10-seco-pregna-5,7-dien-21-yl]-4,4,4-trifluoro-3-trifluoromethyl-3-hydroxy-butyramide

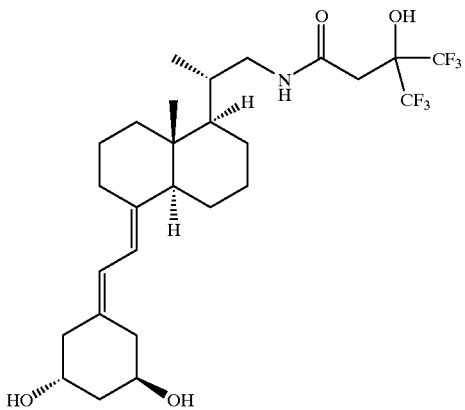

MS: (M)⁺ 555, (M—H₂O )⁺ 537.

NMR (1H, CDCl₃, δ, TMS): 0.77 (s, 3H), 0.97 (d, 3H), 1.39 (s, 3H), 1.1–2.3 (m, 20H), 2.48 (m, 1H), 2.64 (s, 2H), 2.71–2.94 (m, 3H), 3.49 (m, 1H), 4.03 (m, 1H), 4.12 (m, 1H), 5.69 (br t, NH), 5.84 (d, 1H), 6.30 (d, 1H), 7.93 (s, OH).

EXAMPLE 2

2.1. Preparation of 1:1 mixture of (5Z,7E)—(R)—and (S)—N—[(1S,3R,20S)-1,3-Dihydroxy-17a,20a-dihomo-9,10-seco-pregna-5,7,10(19),17-tetraen-21-yl]-4,4,4-trifluoro-3-hydroxy-3-methyl-butyramide a] (1S,4aS,8aR)-[5-((S)-2-Azido-1-methyl-ethyl)-4a-methyl-1,2,3,4,4a,7,8,8a-octahydro-naphthalen-1-yloxy]-tert-butyl-dimethyl-silane

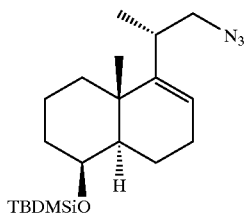

3.0 g (8.85 mmol) of (S)-2-[(4aR,5S,8aS)-5-(tert-Butyl-dimethyl-silanyloxy)-8a-methyl-3,4,4a,5,6,7,8,8a-octahydro-naphthalen-1-yl]-propan-1-ol (preparation described in EP-A 96116735) was dissolved in 25 ml of abs. N,N-dimethylformamide and 15 ml of abs. toluene. 2.53 g (9.65 mmol) of Triphenylphosphine was added, followed by, at 0°, 2.01 ml (10.4 mmol) of diisopropyl azodicarboxylate and 8.85 ml of HN₃ (1.17M, toluene). After 0.5 h the cooling bath was removed and the mixture kept for 18 h at ambient temperature. All solvents were removed and the residue purified by flash chromatography (SiO₂, hexane, hexane/AcOEt=3/1) to yield 2.78 g of the title product as colorless oil besides 624 mg of starting alcohol.

MS: (M—N₂)⁺ 335;

IR: 2095 cm⁻¹.

b] (S)-2-[(4aR,5S,8aS)-5-(tert-Butyl-dimethyl-silanyloxy)-8a-methyl-3,4,4a,5,6,7,8,8a-octahydro-naphthalen-1-yl]-propylamine

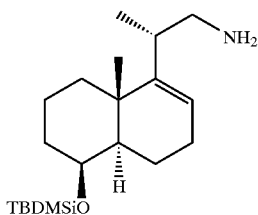

1.51 g (4.15 mmol) of (1S,4aS,8aR)-[5-((S)-2-Azido-1-methyl-ethyl)-4a-methyl-1,2,3,4,4a,7,8,8a-octahydro-naphthalen-1-yloxy]-tert-butyl-dimethyl-silane was dissolved in 4 ml of abs. THF and treated at room temperature with a solution of 1.19 g (4.57 mmol) of triphenylphosphine in 4 ml of abs. THF. The clear solution was kept for 2.5 days at ambient temperature, before it was treated with 2.0 ml of water. After stirring for 0.75 h, the resultant mixture was distributed between water and ether, the organic layer washed with water and brine, dried over magnesium sulfate and evaporated to dryness. Flash chromatography (SiO₂, NEt₃/AcOEt=1/9) afforded 745 mg of the title compound as colorless oil.

MS: (M)⁺ 337.

c] 1:1 Mixture of (R)—and (S)—N—{(S)-2-[(4aR,5S,8aS)-5-(tert-Butyl-dimethyl-silanyloxy)-8a-methyl-3,4,4a,5,6,7,8,8a-octahydro-naphthalen-1-yl]-propyl}-4,4,4-trifluoro-3-hydroxy-3-methyl-butyramide

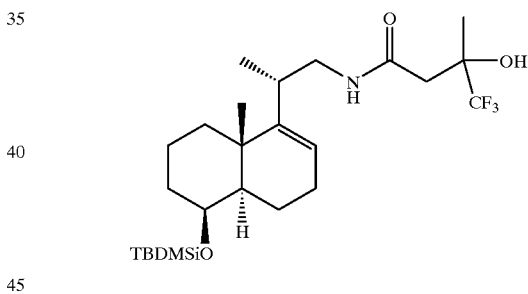

745 mg (2.20 mmol) of (S)-2-[(4aR,5S,8aS)-5-(tert-Butyl-dimethyl-silanyloxy)-8a-methyl-3,4,4a,5,6,7,8,8a-octahydro-naphthalen-1-yl]-propylamine was dissolved in 22 ml of CH₂Cl₂. 567 mg (3.28 mmol) of rac-3-Trifluoromethyl-3-hydroxy-butyric acid and 53 mg (0.2 eq.) of DMAP were added and the solution cooled down to 0°. 724 mg (3.51 mmol) of DCC was added and the cooling bath removed after 20 minutes. 35 Minutes later, starting material had disappeared according to thin layer chromatography. The precipitated urea was filtered off and the filtrate evaporated to dryness. Flash chromatography (SiO₂, hexane/AcOEt=85/15) yielded 1.04 g of the title compound as colorless, viscous oil.

CI-MS: (M+H)⁺ 492.

d] 1:1 Mixture of (R)—and (S)-4,4,4-Trifluoro-3-hydroxy-N—[(S)-2-((4aR,5S,8aS)-5-hydroxy-8a-methyl-3,4,4a,5,6,7,8,8a-octahydro-naphthalen-1-yl)-propyl]-3-methyl-butyramide

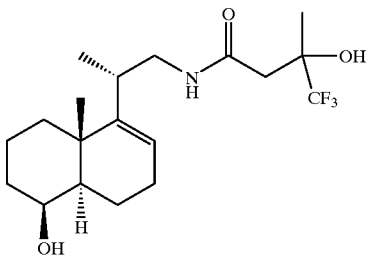

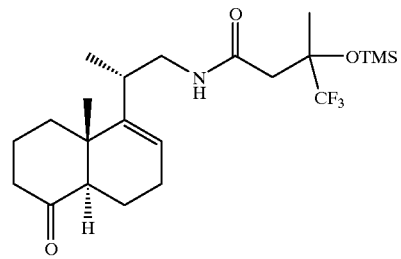

1.47 g (2.98 mmol) of 1:1 Mixture of (R)— and (S)—N—{(S)-2-[(4aR,5S,8aS)-5-(tert-butyl-dimethyl-silanyloxy)-8a-methyl-3,4,4a,5,6,7,8,8a-octahydro-naphthalen-1-yl]-propyl}-4,4,4-trifluoro-3-hydroxy-3-methyl-butyramide was treated with 20 ml of 1M nBu₄NF, which had been dried by stirring over 3Å MS, and kept for 2 days between 55° and 60°. The reaction was quenched by pouring onto crushed ice/NH₄Cl, extracted twice with ether, washed with water and brine, dried over magnesium sulfate and evaporated to dryness. Flash chromatography (SiO₂, hexane/AcOEt=6/4) afforded 896 mg of the title compound as amorphous powder besides 500 mg of starting material in the less polar fractions.

MS: (M)⁺ 377, (M—CH₃)⁺ 362.

e] 1:1 Mixture of (R)- and (S)-4,4,4-Trifluoro-3-hydroxy-3-methyl-N—[(S)-2-((4aR,8aS)-8a-methyl-5-oxo-3,4,4a,5,6,7,8,8a-octahydro-naphthalen-1-yl)-propyl]-butyramide

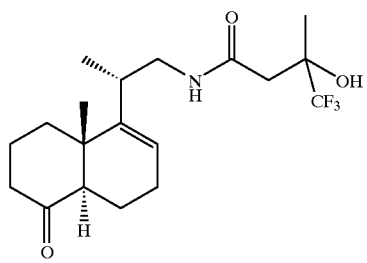

276 mg (0.731 mmol) of 1:1 mixture of (R)- and (S)-4,4,4-trifluoro-3-hydroxy-N-[(S)-2-((4aR,5S,8aS)-5-hydroxy-8a-methyl-3,4,4a,5,6,7,8,8a-octahydro-naphthalen-1-yl)-propyl]-3-methyl-butyramide was dissolved in 12 ml of abs. CH₂Cl₂ and treated at 0° with 830 mg (3 eq.) of PDC (pyridinium-dichromate). After stirring for 2.5 h at ambient temperature the mixture was filtered over a pad of SiO2 (AcOEt) and the solvent removed. Flash chromatography (SiO₂, hexane/AcOEt=6/4) yielded 169 mg of the title compound as colourless oil.

MS: (M)⁺ 375, (M—CH₃)⁺ 360.

f] 1:1 Mixture of (R)- and (S)-4,4,4-Trifluoro-3-methyl-N—[(S)-2-((4aR,8aS)-8a-methyl-5-oxo-3,4,4a,5,6,7,8,8a-octahydro-naphthalen-1-yl)-propyl]-3-trimethylsilanyloxy-butyramide 160 mg (0.426 mmol) of 1:1 Mixture of (R)- and (S)-4,4,4-trifluoro-3-hydroxy-3-methyl-N-[(S)-2-((4aR,8aS)-8a-methyl-5-oxo-3,4,4a,5,6,7,8,8a-octahydro-naphthalen-1-yl)-propyl]-butyramide in 8 ml of abs. CH₂Cl₂ was treated with 0.624 ml (10 eq.) of TMS-imidazole and kept at room temperature for two days. Pouring onto crushed ice, extraction with ether, washing with water, and drying over magnesium sulfate left a crude product, which was purified by flash chromatography (SiO₂, hexane/AcOEt=7/3). Thereby, 156 mg of the title compound was obtained as colourless oil.

MS: (M)⁺ 447, (M—CH₃)⁺ 432.

g] 1:1 Mixture of (R)— and (S)—N—[(S)-2-((E)-(4aS,8aS)-5-{(Z)-2-[3,5-Bis-(tert-butyl-dimethyl-silanyloxy)-2-methylene-cyclohexylidene]-ethylidene}-8a-methyl-3,4,4a,5,6,7,8,8a-octahydro-naphthalen-1-yl)-propyl]-4,4,4-trifluoro-3-methyl-3-trimethylsilanyloxy-butyramide 539 mg (0.942 mmol) of carefully dried (Z)-(3S,5R)-[2-[3,5-bis-(t-butyldimethyl-silanyloxy)-2-methylene-cyclohexylidene]-ethyl]-diphenyl-phosphine oxide was dissolved in 6 ml of abs. THF and treated at −78° with 1.12 ml of secBuLi (1.3M cyclohexane). 30 Minutes later, 207 mg (0.462 mmol) of 1:1 mixture of (R)- and (S)-4,4,4-trifluoro-3-methyl-N—[(S)-2-((4aR,8aS)-8a-methyl-5-oxo-3,4,4a,5,6,7,8,8a-octahydro-naphthalen-1-yl)-propyl]-3-trimethylsilanyloxy-butyramide, dissolved in 4 ml of abs. THF, was added to the deep red solution. The mixture was kept for 1 h at −78° and for 0.5 h at 0°. The discolored reaction mixture was then poured onto crushed ice/NH₄Cl, extracted twice with ether, washed with water, dried over magnesium sulfate, and the solvents carefully removed. Flash chromatography (SiO₂, hexane/AcOEt=9/1 to 6/4) afforded 10 mg of the title compound as colorless oil, besides 139 mg of recovered ketone and 379 recovered phosphine oxide in the more polare fractions.

h] 1:1 Mixture of (5Z,7E)—(R)— and (S)—N—[(1S,3R,20S)-1,3-Dihydroxy-17a,20a-dihomo-9,10-seco-pregna-5,7,10(19),17-tetraen-21-yl]-4,4,4-trifluoro-3-hydroxy-3-methyl-butyramide

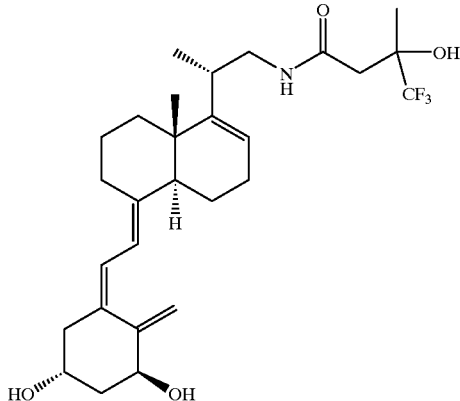

10 mg (0.0123 mmol) of 1:1 mixture of (R)— and (S)—N—[(S)-2-((E)-(4aS,8aS)-5-{(Z)-2-[3,5-bis-(tert-butyl-dimethyl-silanyloxy)-2-methylene-cyclohexylidene]-ethylidene}-8a-methyl-3,4,4a,5,6,7,8,8a-octahydro-naphthalen-1-yl)-propyl]-4,4,4-trifluoro-3-methyl-3-trimethylsilanyloxy-butyramide was treated with 40 equivalents of carefully dried TBAF (1M in THF) at 60° for 2.5 h. The reaction mixture was poured onto crushed ice/NH$_4$Cl, extracted twice with AcOEt, washed with brine, dried over magnesium sulfate and evaporated to dryness. Flash chromatography (SiO$_2$, AcOEt) yielded 5 mg of the title compound as colourless gum.

MS: (M)$^+$ 511, (M—H$_2$O)$^+$ 493;

NMR (1H, CDCl$_3$, δ, TMS): 0.78 (s, 3H), 1.03 (d, 3H), 1.38 (s, 3H), 1.1–2.2 (m, 23H), 2.25–2.4 (m, 3H), 2.47 (d, 1H), 2.60 (br dd, 1H), 2.89 (m, 1H), 3.06 (m, 1H), 3.44 (m, 1H), 4.23 (m, 1H), 4.44 (m, 1H), 5.01 (br s, 1H), 5.35 (br s, 1H), 5.42 (m, 1H), 5.62 (br m, NH), 6.05 (d, 1H), 6.17 (d, OH), 6.37 (d, 1H).

EXAMPLE 2.2

In analogy to example 2.1, but using in step g] (3R,5R)-[2-[3,5-bis-(t-butyldimethyl-silanyloxy)-cyclohexylidene]-ethyl]-diphenyl-phosphine oxide (*Tetrahedron Lett.* 32, 7663 (1991)) was obtained 1:1 Mixture of (E)—(R)— and (S)—N—(1R,3R,20S)-1,3-Dihydroxy-17a,20a-dihomo-19-nor-9,10-seco-pregna-(5,7,17-trien-21-yl)-4,4,4-trifluoro-3-trifluoromethyl-3-hydroxy-3-methyl-butyramide as colourless gum.

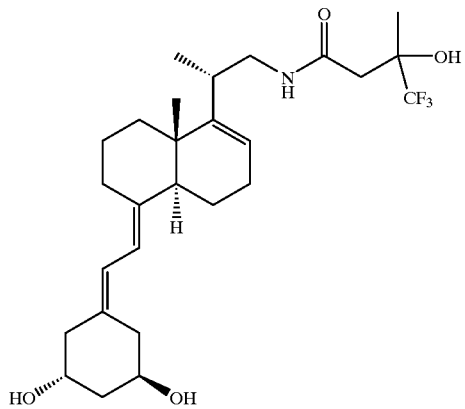

CI-MS: (M+OAc)$^+$ 558, (M—H)$^+$ 498;

NMR (1H, CDCl$_3$, δ, TMS): 0.77 (s, 3H), 1.03 (d, 3H), 1.37 (s, 3H), 1.2–2.55 (m, 28H), 2.7–2.9 (m, 2H), 3.06 (m, 1H), 3.48 (m, 1H), 4.10 (m, 2H), 5.44 (m, 1H), 5.62 (br m, NH), 5.88 (d, 1H), 6.16 (d, OH), 6.32 (d, 1H).

EXAMPLE 3

3.1. Preparation of 1:1 Mixture of —[(5E,7E)—(R)— and —(S)-4,4,4-trifluoro-3-hydroxy-N—[(1S,3R,20S)-1,3-dihydroxy-20-methyl-9,10-seco-pregna-5,7,10(19)-trien-21-yl]-3-methyl-butyramide a] [(1R,3aR,4S,7aR)-1-[(S)-2-Azido-1-methyl-ethyl]-7a-methyl-octahydro-inden-4-yloxy]-tert-butyl-dimethyl-silane

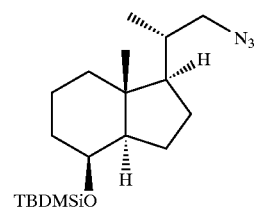

11 g (0.025 mol) of tert-Butyl-[(1R,3aR,4S,7aR)-1-[(S)-2-iodo-1-methyl-ethyl]-7a-methyl-octahydro-inden-4-yloxy]-dimethyl-silane (*J. Org. Chem.* 51, 1269–1272 (1986)) was dissolved in 110 ml of abs. N,N-dimethylformamide and treated with 4.91 g (3 eq.) of NaN$_3$. The mixture was kept for 4.5 h at 60° and the progress of the reaction monitored by thin layer chromatography. Cooling to room temperature, pouring onto crushed ice, twofold extraction with hexane, washing with NaHCO$_3$ and drying over sodium sulfate left 9 g of a crude product, which was pure according to 250 MHz NMR and used as such for the next step.

MS: (M—N$_2$)$^+$ 323.

b] (S)-2-[(1R,3aR,4S,7aR)-4-(tert-Butyl-dimethyl-silanyloxy)-7a-methyl-octahydro-inden-1-yl]-propylamine

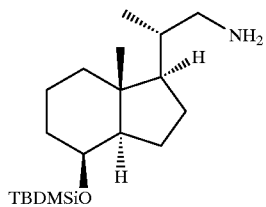

9 g of[(1R,3aR,4S,7aR)-1-[(S)-2-Azido-1-methyl-ethyl]-7a-methyl-octahydro-inden-4-yloxy]-tert-butyl-dimethyl-silane was dissolved in 100 ml of AcOEt and hydrogenated over 0.9 g of 10% Pd/C, which was added in three portions, during 8 h at ambient temperature and 1 atm of $H_2$. After filtration over a pad of Celite the solvents were removed. Flash chromatography ($SiO_2$, AcOEt/$NEt_3$=95/5) produced 7.2 g of the title compound as slightly brown oil.

MS: $(M+H)^+$ 326.

c] 1:1 Mixture of (R)— and (S)—N—[(S)-2-[(1R,3aR,4S,7aR)-4-(tert-butyl-dimethyl-silanyloxy)-7a-methyl-octahydro-inden-1-yl]-propyl]-4,4,4-trifluoro-3-hydroxy-3-methyl-butyramide

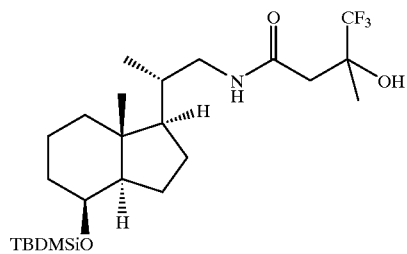

1 g (3 mmol) of (S)-2-[(1R,3aR,4S,7aR)-4-(tert-Butyl-dimethyl-silanyloxy)-7a-methyl-octahydro-inden-1-yl]-propylamine, 0.51 g (1 eq.) of rac-3-trifluoromethyl-3-hydroxy-butyric acid, and 0.36 g (1.1 eq.) of DMAP were dissolved in 20 ml of $CH_2Cl_2$. At 0° 0.69 g (1.1 eq.) of EDCI was added and the mixture allowed to react for 4 h at ambient temperature. The solution was washed with citric acid and evaporated to dryness. Flash chromatography ($SiO_2$, hexane/AcOEt=85/15) yielded 953 mg of the title compound as colorless oil.

MS: $(M+H)^+$ 480.

d] 1:1 Mixture of (R)- and (S)-4,4,4-trifluoro-3-hydroxy-N—[(S)-2-[(1R,3aR,4S,7aR)-4-hydroxy-7a-methyl-octahydro-inden-1-yl]-propyl]-3-methyl-butyramide

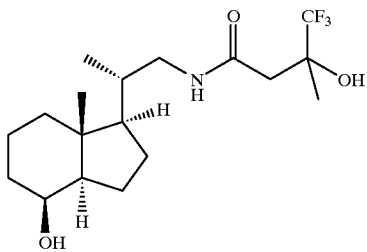

0.95 g of 1:1 Mixture of (R)— and (S)—N—[(S)-2-[(1R,3aR,4S,7aR)-4-(tert-butyl-dimethyl-silanyloxy)-7a-methyl-octahydro-inden-1-yl]-propyl]-4,4,4-trifluoro-3-hydroxy-3-methyl-butyramide was dissolved in a mixture of 1 ml THF and 4 ml of $CH_3CN$ at room temperature. 2 ml of aq. HF-solution (40%) was added and the reaction monitored by thin layer chromatography. After completion of the deprotection, the reaction mixture was neutralized with $NaHCO_3$, extracted with $Et_2O$, dried over $Na_2SO_4$ and carefully evaporated. 0.37 g of the pure title compound was obtained as colourless oil.

MS: $(M+H)^+$ 366.

e] 1:1 Mixture of (R)- and (S)-4,4,4-trifluoro-3-hydroxy-3-methyl-N—[(S)-2-[(1R,3aR,7aR)-7a-methyl-4-oxo-octahydro-inden-1-yl]-propyl]-butyramide

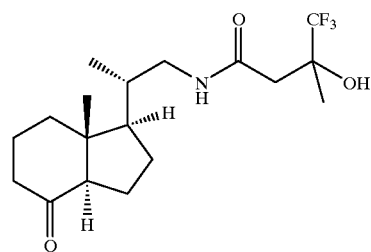

0.37 g (1 mmol) of 1:1 Mixture of (R)- and (S)-4,4,4-trifluoro-3-hydroxy-N—[(S)-2-[(1R,3aR,4S,7aR)-4-hydroxy-7a-methyl-octahydro-inden-1-yl]-propyl]-3-methyl-butyramide was dissolved in 5 ml of abs. $CH_2Cl_2$ and reacted with 760 mg (2 eq.) of PDC (pyridinium-dichromate). After stirring for 2.5 h at ambient temperature the mixture was filtred over a pad of Celite and the solvent removed. Flash chromatography ($SiO_2$, hexane/AcOEt=7/3) yielded 112 mg of the title compound as colourless oil.

MS: $(M)^+$ 364.

f] 1:1 Mixture of (R)- and (S)-4,4,4-trifluoro-3-methyl-N—[(S)-2-[(1R,3aR,7aR)-7a-methyl-4-oxo-octahydro-inden-1-yl]-propyl]-3-trimethylsilanyloxy-butyramide

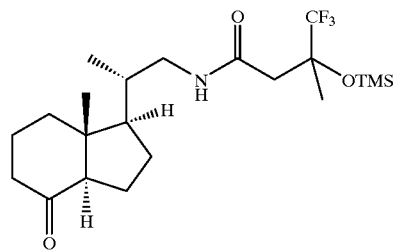

200 mg (0.55 mmol) of 1:1 Mixture of (R)- and (S)-4,4,4-trifluoro-3-hydroxy-3-methyl-N—[(S)-2-[(1R,3aR,7aR)-7a-methyl-4-oxo-octahydro-inden-1-yl]-propyl]-butyramide in 5 ml of abs. $CH_2Cl_2$ was treated with 0.438 ml (6 eq.) of TMS-imidazole and kept at room temperature over night. A second portion of 0.438 ml of TMS-imidazole was added and the reaction allowed to proceed for two days. Pouring onto crushed ice, extraction with ether, washing with water, and drying over sodium sulfate left a crude product, which was purified by flash chromatography ($SiO_2$, hexane/AcOEt=8/2). Thereby, 160 mg of the title compound was obtained as white foam.

MS: (M)+ 435.

g] 1:1 Mixture of (5E,7E)—(R)— and —(S)—N—[(1S,3R,20S)-1,3-bis-(tert-butyl-dimethyl-silanyloxy)-20-methyl-9,10-seco-pregna-5,7,10(19)-trien-21-yl]-4,4,4-trifluoro-3-methyl-3-trimethylsilanyloxy-butyramide

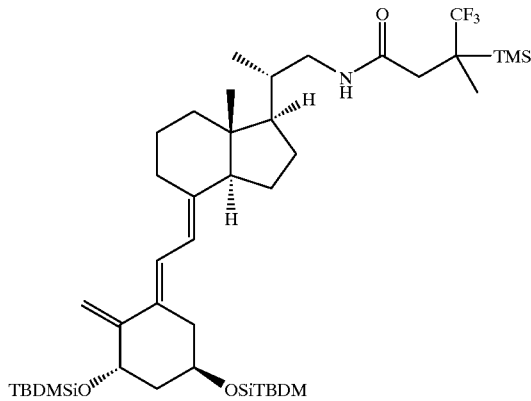

580 mg of carefully dried (E)—(3S,5R)-[2-[3,5-bis-(tert-butyl-dimethyl-silanyloxy]-2-methylene-cyclohexylidene]-ethyl]-diphenyl-phosphine oxide (preparation see example 7 below) was dissolved in 10 ml of abs. THF and treated at −78° with 0.62 ml of nBuLi (1.5M, hexane). 15 Minutes later, 160 mg (0.334 mmol) of 1:1 Mixture of (R)- and (S)-4,4,4-trifluoro-3-methyl-N—[(S)-2-[(1R,3aR,7aR)-7a-methyl-4-oxo-octahydro-inden-1-yl]-propyl]-3-trimethylsilanyloxy-butyramide, dissolved in 1.5 ml of abs. THF, was added to the deep red solution. The mixture was kept for 0.25 h at −78° and for 1 h at 0°. The discolored reaction mixture was then poured onto crushed ice, extracted twice with ether, washed with water, dried over sodium sulfate, and the solvents carefully removed. Flash chromatography (SiO₂, hexane/AcOEt=9/1) afforded 70 mg of the title compound as colorless oil.

MS: (M+H)+ 801.

h] 1:1 Mixture of[(5E,7E)—(R)— and —(S)-4,4,4-trifluoro-3-hydroxy-N—[(1S,3R,20S)-1,3-dihydroxy-20-methyl-9,10-seco-pregna-5,7,10(19)-trien-21-yl]-3-methyl-butyramide

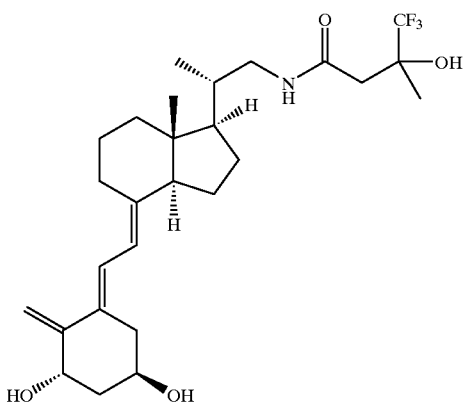

70 mg (0.08 mmol) of 1:1 Mixture of (5E,7E)—(R)— and —(S)—N—[(1S,3R,20S)-1,3-bis-(tert-butyl-dimethyl-silanyloxy)-20-methyl-9,10-seco-pregna-5,7,10(19)-trien-21-yl]-4,4,4-trifluoro-3-methyl-3-trimethylsilanyloxy-butyramide was treated with 8 equivalents of carefully dried TBAF (0.2M in THF) at 40° for 2 h. The reaction mixture was poured onto crushed ice, extracted twice with AcOEt, washed with water, dried over sodium sulfate and evaporated to dryness. Flash chromatography (SiO₂, AcOEt) yielded 61 mg of the title compound as white foam.

MS: (M+H)+ 500.

NMR (1H, CDCl₃, δ, TMS): 0.59 (s, 3H), 0.99 (d, 3H), 1.41 (s, 3H), 1.0–2.15 (m, 16H), 2.29 (dt; 1H), 2.46&2.54 (d(AB); 2H), 2.86 (m, 2H), 2.95–3.50 (m, 2H), 4.25 (m, 1H), 4.52 (m, 1H), 5.02 (s br; 1H), 5.15 (s br; 1H), 5.64 (br s, OH), 5.89 (d, 1H), 6.11(br t, NH), 6.55 (d, 1H).

EXAMPLE 4

4.1. Preparation of 1:1 Mixture of (E)—(R)— and (S)—N—[(1R,3R,20S)-1,3-dihydroxy-20-methyl-19-nor-9,10-seco-pregna-5,7-dien-21-yl]-4,4,4-trifluoro-3-hydroxy-20-methyl-butyramide a] Methanesulfonic acid (E)—(1R,3R,20S)-1,3-bis-(tert-butyl-dimethyl-silanyloxy)-20-methyl-19-nor-9,10-seco-pregna-5,7-dien-21-yl ester

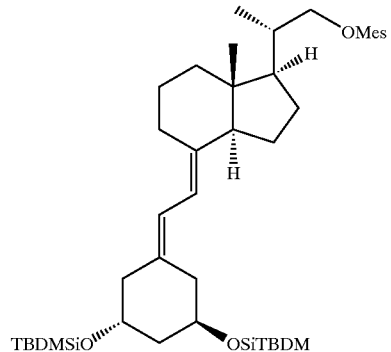

wherein Mes signifies —SO₂CH₃

2.8 g (0.005 mol) of (E)—(1R,3R,20S)-1,3-Bis-(tert-butyl-dimethyl-silanyloxy)-20-methyl-19-nor-9,10-seco-pregna-5,7-dien-21-ol (*Tetrahedron Letters* 33, 2937–2940 (1992)) and 0.89 g of DMAP (1.5 eq) were dissolved in 50 ml of CH₂Cl₂ at 0° C. and, under argon, 0.84 g of mesylchloride (1.5 eq) was added and the solution was stirred at room temperature over night. The reaction mixture was extracted with an aqueous solution of citric acid. The organic phase was dried over sodium sulfate and evaporated to yield 3.39 g of crude product which was pure according to 250 MHz NMR and used as such for the next step.

MS: (M)+ 640.

b] (E)—(1R,3R,20S)-21-Azido-(1,3-bis-(tert-butyl-dimethyl-silanyloxy)-20-methyl-19-nor-9,10-seco-pregna-5,7-diene

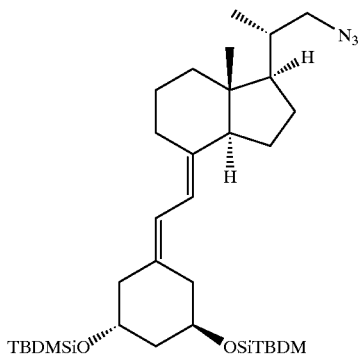

2.9 g (0.0045 mol) of Methanesulfonic acid (E)—(1R, 3R,20S)-1,3-bis-(tert-butyl-dimethyl-silanyloxy)-20-methyl-19-nor-9,10-seco-pregna-5,7-dien-21-yl ester was dissolved in 50 ml of DMF. 0.88 g of sodium azide (3 eq) was added and the reaction mixture was heated at 60° C. for two hours. The solvent was evaporated and the residue was dissolved in hexane and washed three times with water. The organic phase was dried over sodium sulfate and evaporated. Flash chromatography (SiO$_2$, hexane/AcOEt=19.5/0.5) afforded 2.27 g of the title compound as colorless oil

MS: (M)$^+$ 587.

c] (E)—(1R,3R,20S)-[1,3-Bis-(tert-butyl-dimethyl-silanyloxy)-20-methyl-19-nor-9,10-seco-pregna-5,7-dien-21-yl]-amine

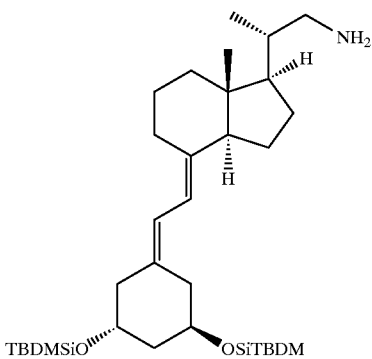

0.588 g ( 0.01 mol) of (E)—(1R,3R,20S)-21-Azido-(1,3-bis-(tert-butyl-dimethyl-silanyloxy)-20-methyl-19-nor-9, 10-seco-pregna-5,7-diene and 0.393 g (1.5 eq) of PPh$_3$ were dissolved in 5 ml of THF. 0.027 ml of water (1.5 eq) was slowly added under stirring. The reaction mixture was heated at 60° C. over night, then evaporated to dryness. The residue was dissolved in dry hexane and the insoluble PPh3O was filtered off. 0.69 g of the title compound was obtained after evaporation of the filtrate, and used as such for the next step.

d] 1:1 Mixture of (E)—(R)— and (S)—N—[(1R,3R, 20S)-1,3-bis-(tert-butyl-dimethyl-silanyloxy)-20-methyl-19-nor-9,10-seco-pregna-5,7-dien-21-yl]-4,4,4-trifluoro-3-hydroxy-20-methyl-butyramide

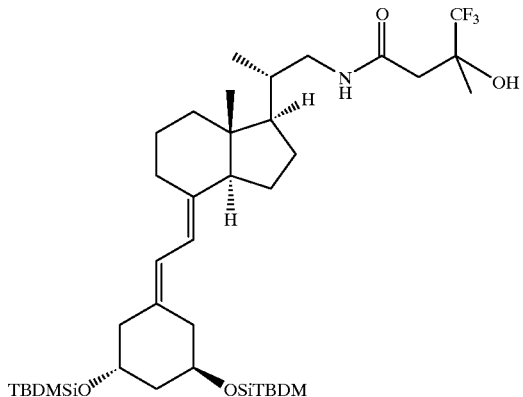

0.152 g (0.26 mmol) of (E)—(1R,3R,20S)-[1,3-Bis-(tert-butyl-dimethyl-silanyloxy)-20-methyl-19-nor-9,10-seco-pregna-5,7-dien-21-yl]-amine, 0.045 g (1 eq) of 4,4,4-trifluoro-3-hydroxy-3-methyl-butyric acid, 0.059 g (1 eq) of EDCI, and 0.030 g (1.1 eq) of DMAP were dissolved in 5 ml of CH$_2$Cl$_2$ at 0° C. The reaction mixture was stired over night at room temperature, evaporated, dissolved in AcOEt and washed with water and with an aqueous solution of citric acid. The organic phase was dried over sodium sulfate and evaporated. Flash chromatography (SiO$_2$, hexane/AcOEt= 98/2) afforded 20 mg of the title compound as colorless oil

MS: (M+H)$^+$ 716.

e] 1:1 Mixture of (E)—(R)— and (S)—N—[(1R,3R, 20S)-1,3-dihydroxy-20-methyl-19-nor-9,10-seco-pregna-5, 7-dien-21-yl]-4,4,4-trifluoro-3-hydroxy-3-methyl-butyramide

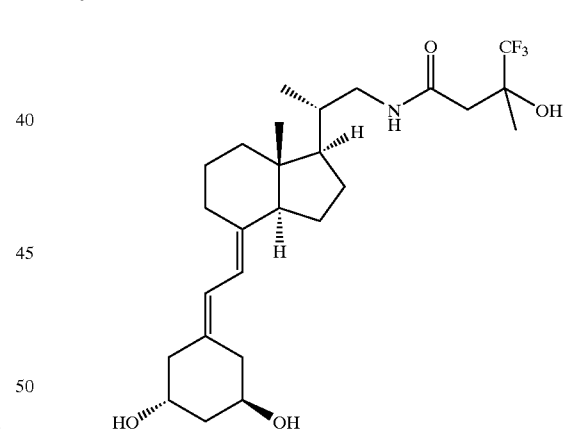

0.08 g (0.1 mmol) of 1:1 Mixture of (E)—(R)— and (S)—N—[(1R,3R,20S)-1,3-bis-(tert-butyl-dimethyl-silanyloxy)-20-methyl-19-nor-9,10-seco-pregna-5,7-dien-21-yl]-4,4,4-trifluoro-3-hydroxy-3-methyl-butyramide and 3 equivalents of TBAF were dissolved in 2 ml of dry THF. The reaction mixture was stirred over night at room temperature and evaporated. Flash chromatography (SiO$_2$, iso-propanol/AcOEt=1/19) afforded 28 mg of the title compound as colorless oil

MS: (M+H)$^+$ 488.

NMR (1H, CDCl$_3$, δ, TMS): 0.57 (s, 3H), 1.02 (d, 3H), 1.41 (s, 3H), 1.20–2.03 (m, 16H), 2.24 (m; 2H), 2.46&2.54 (d(AB); 2H), 2.49 (m; 1H), 2.79 (m, 2H), 3.06 (m, 1H), ), 3.40 (m, 1H), 4.09 (m, 2H), 5.14 (m br; N—H), 5.88 (d, 1H), 6.09&6.12(2s, OH), 6.32 (d, 1H).

EXAMPLE 4.2

In analogy to example 4.1., but using in step d] 4,4,4-trifluoro-3-hydroxy-3-trifluoromethyl-butyric acid as coupling partner was obtained as colorless gum (E)—(1R,3R,20S)—N-(1,3-Dihydroxy-20-methyl-19-nor-9,10-seco-pregna-5,7-dien-21-yl)-4,4,4-trifluoro-3-hydroxy-3-trifluoromethyl-butyramide

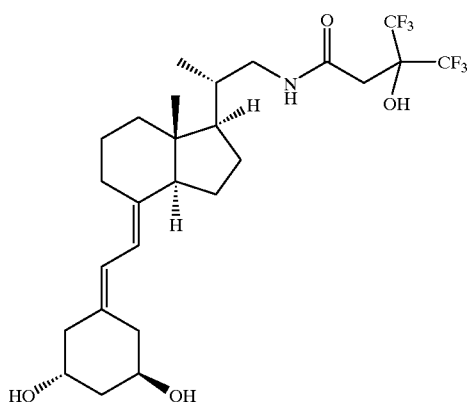

MS: (M)+ 541.

NMR (1H, CDCl₃, δ, TMS): 0.57 (s, 3H), 0.99 (d, 3H), 1.11–2.07 (m, 16H), 2.24 (m; 2H), 2.50 (m; 1H), 2.69 (s; 2H), 2.77 (m, 1H), 3.11 (m, 1H), ), 3.41 (m, 1H), 4.09 (m, 2H), 5.78 (m br; N—H), 5.87 (d, 1H), 6.33 (d, 1H), 7.97 (s, OH).

EXAMPLE 4.3

In analogy to example 4.1., but using in step d] 3-(1-hydroxy-1-methyl-ethyl)-benzoic acid as coupling partner was obtained as colorless gum (E)—(1R,3R,20S)—N-(1,3-Dihydroxy-20-methyl-19-nor-9,10-seco-pregna-5,7-dien-21-yl)-3-(1-hydroxy-1-methyl-ethyl)-benzamide

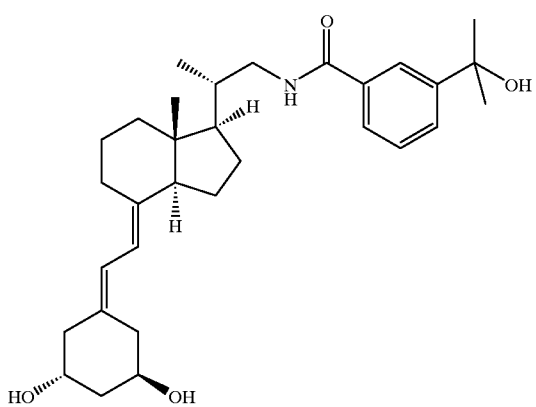

MS: (M)+ 495.

NMR (1H, CDCl₃, δ, TMS): 0.59 (s, 3H), 1.06 (d, 3H), 1.21–2.10 (m, 17H), 1.61 (s; 6H), 2.24 (m; 2H), 2.50 (m; 1H), 2.59 (m; 2H), 3.23 (m, 1H), ), 3.57 (m, 1H), 4.09 (m, 2H), 5.88 (d, 1H), 6.14 (t br; N—H), 6.32 (d, 1H),7.42 (t, 1H), 7.62 (dm, 2H), 7.94 (s br, 1H).

EXAMPLE 4.4

In analogy to example 4.1., but using in step d] 2,2-dimethyl-propionic acid as coupling partner was obtained as colorless gum (E)—(1R,3R,20S)—N-(1,3-Dihydroxy-20-methyl-19-nor-9,10-seco-pregna-5,7-dien-21-yl)-2,2-dimethyl-propionamide

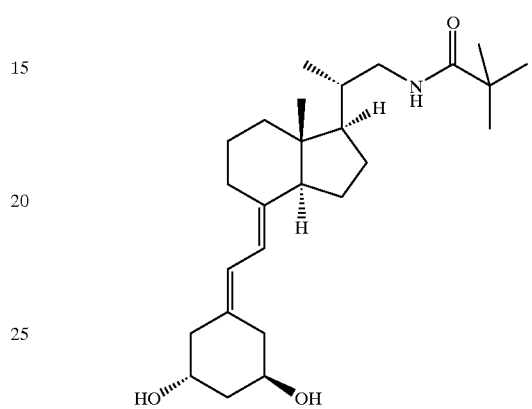

MS: (M)+ 417.

NMR (1H, CDCl₃, δ, TMS): 0.56 (s, 3H), 0.96 (d, 3H), 1.20 (s; 9H), 1.19–2.03 (m, 16H), 2.23 (m; 2H), 2.50 (m; 1H), 2.78 (m; 2H), 2.95 (m, 1H),), 3.37 (m, 1H), 4.09 (m, 2H), 5.64 (t br; N—H), 5.89 (d, 1H), 6.32 (d, 1H).

EXAMPLE 4.5

In analogy to example 4.1., but using in step d] 2-hydroxy-2-methyl-propionic acid as coupling partner was obtained as colorless gum (E)—(1R,3R,20S)—N-(1,3-Dihydroxy-20-methyl-19-nor-9,10-seco-pregna-5,7-dien-21-yl)-2-hydroxy-2-methyl-propionamide

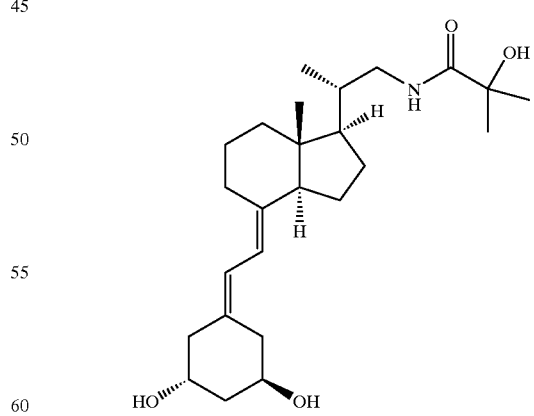

MS: (M)+ 419.

NMR (1H, CDCl₃, δ, TMS): 0.57 (s, 3H), 0.98 (d, 3H), 1.47 (s; 6H), 1.22–2.08 (m, 16H), 2.21 (m; 2H), 2.49 (m; 1H), 2.79 (m; 2H), 3.03 (m, 1H), ), 3.45 (m, 2H), 4.09 (m, 2H), 5.88 (d, 1H), 6.33 (d, 1H), 6.70 (t br; N—H).

EXAMPLE 4.6

In analogy to example 4.1., but using in step a] (5Z,7E)-(3S,20S)-3-(tert-Butyl-dimethyl-silanyloxy)-20-methyl-9,10-seco-pregna-5,7,10(19)-trien-21-ol (EP 78704 A1) as starting material was obtained as colorless gum 1:1 Mixture of (5Z,7E)—(R)— and—(S)-4,4,4-trifluoro-3-hydroxy-N—[(3S,20S)-3-hydroxy-20-methyl-9,10-seco-pregna-5,7,10(19)-trien-21-yl]-butyramide

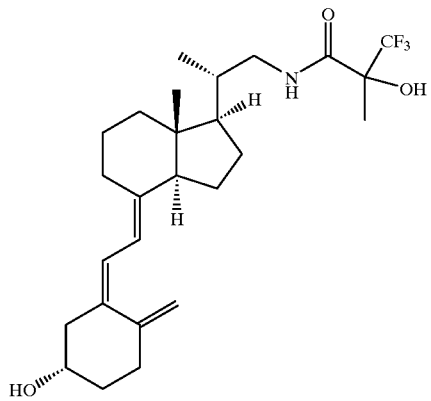

MS: (M)+ 483.

EXAMPLE 4.7

In analogy to example 4.1 but using in step d) optically pure (R)-4,4,4-trifluoro-3-hydroxy-3-methyl-butyric acid as coupling partner was obtained as a white solid E—(R)—N—[(1R,3R,20S)-1,3-dihydroxy-20-methyl-19-nor-9,10-seco-pregna-5,7-dien-21-yl]-4,4,4-trifluoro-3-hydroxy-3-methyl-butyramid.

The starting acid was prepared by preparative HPLC of the corresponding methyl ester on a chiral column followed by saponification.

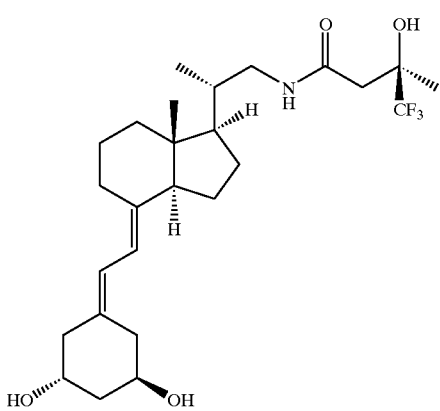

MS: (M+H)+ 488.

EXAMPLE 5

5.1. Preparation of 1:1 Mixture of [(5Z,7E)—(R)— and (S)—N—[(1S,3R,20S)-1,3-dihydroxy-20-methyl-9,10-seco-pregna-5,7,10(19)-trien-21-yl]-4,4,4-trifluoro-3-hydroxy-3 -methyl-butyramide a] (5Z,7E)—(1S,3R,20S)-21-Azido-1,3-bis-(tert-butyl-dimethyl-silanyloxy)-20-methyl-9,10-seco-pregna-5,7,10 (19)-triene

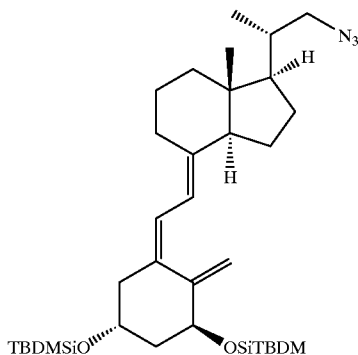

0.5 g (0.87 mmol) of (5Z,7E)—(1S,3R,20S)-1,3-Bis-(tert-butyl-dimethyl-silanyloxy)-20-methyl-9,10-seco-pregna-5,7,10(19)-trien-21-ol (*J. Org. Chem.* 53, 3450–3457 (1988)), 0.53 g (2 eq) of $Zn(N_3)_2 \cdot 2Py$ complex and 0.45 g (2 eq) of $PPh_3$ were dissolved in 10 ml toluol. 0.26 ml (2 eq) of DEAD was slowly added and the reaction mixture stirred over night at room temperature and then heated to 60° C. for one additional hour. The solution was treated with a mixture of methanol/water (7/3) and extracted with hexane. The organic phase was dried over sodium sulfate and evaporated. Flash chromatography ($SiO_2$, hexane/AcOEt=19.5/0.5) afforded 0.262 g of 1-(2-azido-1-methyl-ethyl)-4-{2-[3,5-bis-(tert-butyl-dimethyl-silanyloxy)-2-methylene-cyclohexylidene]-ethylidene}-7a-methyl-octahydro-indene as a colorless oil

MS: (M)+ 599.

b] In analogy to example 4.1., but using in step c] (5Z,7E)—(1S,3R,20S)-21-Azido-1,3-bis-(tert-butyl-dimethyl-silanyloxy)-20-methyl-9,10-seco-pregna-5,7,10 (19)-triene as starting material was obtained as colorless gum 1:1 Mixture of [(5Z,7E)—(R)— and (S)—N—[(1S,3R,20S)-1,3-dihydroxy-20-methyl-9,10-seco-pregna-5,7,10 (19)-trien-21-yl]-4,4,4-trifluoro-3-hydroxy-3-methyl-butyramide

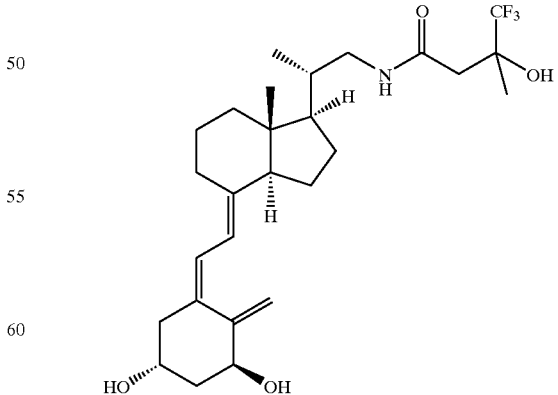

MS: (M)+ 499.

NMR (1H, $CDCl_3$, δ, TMS): 0.56 (s, 3H), 0.98 (d, 3H), 1.41 (s; 3H), 1.13–2.10 (m, 15H), 2.34 (dd; 1H), 2.41&2.57

(d(AB), 2H), 2.61 (m; 1H), 2.77–3.17 (m; 2H), 3.40 (m, 1H), 4.00 (m, 1H), 4.46 (m, 1H), 5.01 (s br, 1H), 5.35 (s br, 1H), 5.63 (m; N—H), 6.03 (d, 1H), 6.09&6.14 (2s, 1H), 6.39 (d, 1H).

EXAMPLE 6

6.1. Preparation of 1:1 Mixture of (E)—(R)— and (S)—N—[(1R,3R,20R)-1,3-dihydroxy-20-methyl-19-nor-9,10-seco-pregna-5,7-dien-21-yl]-4,4,4-trifluoro-3-hydroxy-3-methyl-butyramide a] 2,2-Dimethyl-propionic acid (E)—(1R,3R,20R)-1,3-bis-(tert-butoxy-dimethyl-silanyloxy)-20-methyl-19-nor-9,10-seco-pregna-5,7-dien-21-yl ester

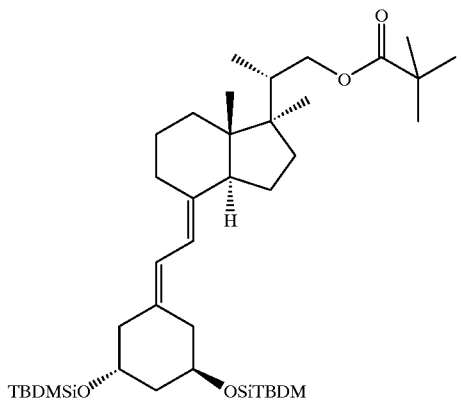

2 g (3.6 mmol) of (3R,5R)-[2-[3,5-Bis-(tert-Butyl-dimethyl-silanyloxy)-cyclohexylidene]-ethyl]-diphenyl-phosphine oxide (*Tetrahedron Lett.* 33, 2937–40 (1992)) was dissolved in 5 ml of dry THF at −78° C. and one equivalent of BuLi in hexane was slowly added. After half an hour, 0.6 g (2 mmol) of 2,2-dimethyl-propionic acid (R)-2-[(1R,3aR,7aR)-7a-methyl-4-oxo-octahydro-inden-1-yl]-propyl ester (PCT Int. Appl. WO 9622776) in 2.5 ml THF was slowly added to the deep red solution and the mixture was allowed to warm to room temperature under stirring over night. After quenching with an aqueous solution of ammonium chloride, the THF was distilled of and the residue was extracted with ether, dried over sodium sulfate and the ether was removed. Flash chromatography (SiO$_2$, hexane/AcOEt=9/1) afforded 1.11 g of 2,2-dimethyl-propionic acid (E)—(1R,3R,20R)-1,3-bis-(tert-butoxy-dimethyl-silanyloxy)-20-methyl-19-nor-9,10-seco-pregna-5,7-dien-21-yl ester as colorless oil.

MS: (M)$^+$ 646.

b] (E)—(1R,3R,20R)-1,3-Bis-(tert-butoxy-dimethyl-silanyloxy)-20-methyl-19-nor-9,10-seco-pregna-5,7-dien-21-ol

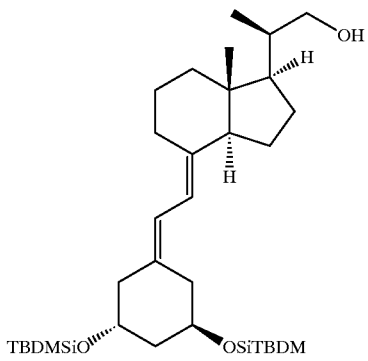

2.83 ml (2 eq) of a solution of diisobutylaluminumhydride (1.2 molar in toluene) was slowly added to a solution of 1.1 g (1.7 mmol) of 2,2-dimethyl-propionic acid (E)—(1R,3R,20R)-1,3-bis-(tert-butoxy-dimethyl-silanyloxy)-20-methyl-19-nor-9,10-seco-pregna-5,7-dien-21-yl ester in 2 ml of toluene at −78° C. After one hour at this temperature the reaction mixture was stirred for two additional hours at room temperature before quenching with 8 ml of MeOH. The desired alcohol was extracted with AcOEt, dried over sodium sulfate, and the organic solvent was removed. Flash chromatography (SiO$_2$, hexane/AcOEt=8/2) afforded 0.69 g of (E)—(1R,3R,20R)-1,3-bis-(tert-butoxy-dimethyl-silanyloxy)-20-methyl-19-nor-9,10-seco-pregna-5,7-dien-21-ol as colorless oil.

MS: (M)$^+$ 562.

c] In analogy to example 4.1., but using in step a] (E)—(1R,3R,20R)-1,3-Bis-(tert-butoxy-dimethyl-silanyloxy)-20-methyl-19-nor-9,10-seco-pregna-5,7-dien-21-ol was obtained as colorless foam 1:1 Mixture of (E)—(R)— and (S)—N—[(1R,3R,20R)-1,3-dihydroxy-20-methyl-19-nor-9,10-seco-pregna-5,7-dien-21-yl]-4,4,4-trifluoro-3-hydroxy-3-methyl-butyramide

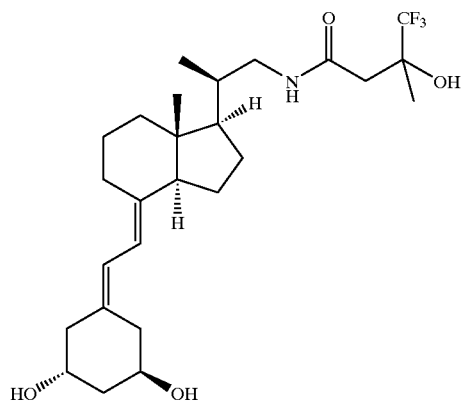

MS: (M+H)$^+$ 488.

NMR (1H, CDCl$_3$, δ, TMS): 0.60 (s, 3H), 0.91 (d, 3H), 1.41 (s; 3H), 1.20–2.03 (m, 15H), 2.21 (m; 2H), 2.41&2.57 (d(AB), 2H), 2.49 (m; 1H), 2.79 (m; 2H), 2.95 (m,1H), 3.64 (m, 1H+OH), 4.09 (m, 2H), 5.65 (m; N—H), 5.88 (d, 1H), 6.06&6.08 (2s, 1H: OH), 6.32 (d, 1H).

EXAMPLE 6.2

During the synthesis of example 6.1., in analogy to example 4.1., it was possible at the stage of step d] which consists of acylation of the amine with racemic 4,4,4-trifluoro-3-hydroxy-3-methyl-butyric acid to separate the two corresponding epimers, namely the 1:1 mixture of (E)—(R)— and (S)—N—[(1R,3R,20R)-1,3-bis-(tert-butyl-dimethyl-silanyloxy)-20-methyl-19-nor-9,10-seco-pregna-5,7-dien-21-yl]-4,4,4-trifluoro-3-hydroxy-20-methyl-butyramide using column chromatography In analogy to example 4.1., but using in step e] the less polar epimer of (E)—(R)— or (S)—N—[(1R,3R,20R)-1,3-bis-(tert-butyl-dimethyl-silanyloxy)-20-methyl-19-nor-9,10-seco-pregna-5,7-dien-21-yl]-4,4,4-trifluoro-3-hydroxy-20-methyl-butyramide was obtained as a colorless foam (E)—(R)— or (S)—N—[(1R,3R,20R)-1,3-dihydroxy-20-methyl-19-nor-9,10-seco-pregna-5,7-dien-21-yl]-4,4,4-trifluoro-3-hydroxy-3-methyl-butyramide

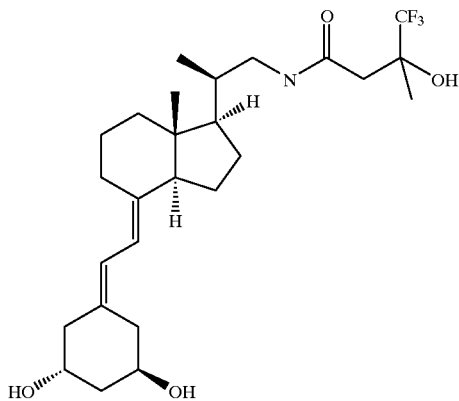

NMR (1H, CDCl$_3$, δ, TMS): 0.60 (s, 3H), 0.91 (d, 3H), 1.41 (s; 3H), 1.20–2.06 (m, 16H), 2.17 (m; 2H), 2.41&2.57 (d(AB), 2H), 2.49 (m; 1H), 2.76 (m; 2H), 2.98 (m,1H), 3.65 (m, 1H), 4.09 (m, 2H), 5.65 (m; N—H), 5.88 (d, 1H), 6.32 (m br, OH), 6.32 (d, 1H).

EXAMPLE 6.3

During the synthesis of example 6.1., in analogy to example 4.1., it was possible at the stage of step d] which consists of acylation of the amine with racemic 4,4,4-trifluoro-3-hydroxy-3-methyl-butyric acid to separate the two corresponding epimers, namely the 1:1 mixture of (E)—(R)— and (S)—N—[(1R,3R,20R)-1,3-bis-(tert-butyl-dimethyl-silanyloxy)-20-methyl-19-nor-9,10-seco-pregna-5,7-dien-21-yl]-4,4,4-trifluoro-3-hydroxy-20-methyl-butyramide using column chromatography.

In analogy to example 4.1., but using in step e] the more polar epimer of (E)—(R)— or (S)—N—[(1R,3R,20R)-1,3-bis-(tert-butyl-dimethyl-silanyloxy)-20-methyl-19-nor-9,10-seco-pregna-5,7-dien-21-yl]-4,4,4-trifluoro-3-hydroxy-20-methyl-butyramide was obtained as colorless foam (E)—(S)— or (R)—N—[(1R,3R,20R)-1,3-dihydroxy-20-methyl-19-nor-9,10-seco-pregna-5,7-dien-21-yl]-4,4,4-trifluoro-3-hydroxy-3-methyl-butyramide NMR (1H, CDCl$_3$, δ, TMS): 0.60 (s, 3H), 0.91 (d, 3H), 1.40 (s; 3H), 1.20–2.03 (m, 15H), 2.21 (m; 2H), 2.41&2.58 (d(AB), 2H), 2.49 (m; 1H), 2.79 (m; 2H), 2.94 (m,1H), 3.66 (m, 1H), 4.09 (m, 2H), 5.64 (m; N—H), 5.88 (d, 1H), 6.06 (s, OH), 6.31 (d, 1H).

EXAMPLE 6.4 a] In analogy to example 6.1., but using in step a] (Z)—(S)—[2-[5-(tert-Butyl-dimethyl-silanyloxy)-2-methylene-cyclohexylidene]-ethyl]-diphenyl-phosphine oxide (Perkin I, 1974, 2005–2009; J. Org. Chem, 48, 1414–1417 (1983)) was obtained as colorless oil (5Z,7E)—(3S,20R)-3-(tert-Butyl-dimethyl-silanyloxy)-20-methyl-9,10-seco-pregna-5,7-dien-21-ol

MS: (M)$^+$ 444.

b] In analogy to example 4.1., but using in step a] (5Z,7E)-(3S,20R)-3-(tert-Butyl-dimethyl-silanyloxy)-20-methyl-9,10-seco-pregna-5,7-dien-21-ol was obtained as colorless foam 1:1 Mixture of (5Z,7E)—(R)— and (S)—N—[(3S,20R)-3-hydroxy-20-methyl-9,10-seco-pregna-5,7,10(19)-trien-21-yl]-4,4,4-trifluoro-3-hydroxy-3-methyl-butyramide

MS: (M+H)$^+$ 484.

NMR (1H, CDCl$_3$, δ, TMS): 0.60 (s, 3H), 0.90 (d, 3H), 1.40 (s; 3H), 1.20–2.38 (m, 19H), 2.40&2.58 (d(AB), 2H), 2.91 (m; 2H), 3.67 (m, 1H), 3.96 (m, 1H), 4.82 (s br, 1H), 5.06 (s br, 1H), 5.76 (m; N—H), 6.05 (d, 1H), 6.09 (s, OH), 6.23 (d, 1H).

EXAMPLE 6.5 a] In analogy to example 6.1., but using in step a] (Z)—(3S,5R)-[2-[3,5-bis-(tert-butyl-dimethyl-silanyloxy)-2-methylene-cyclohexylidene]-ethyl]-diphenyl-phosphine oxide (J. Org. Chem. 51, 3098–3108 (1997)) was obtained as colorless oil (5Z,7E)—(1S,3R,20R)-1,3-bis-(tert-butyl-dimethyl-silanyloxy)-20-methyl-9,10-seco-pregna-5,7,10(19)-trien-1-ol

MS: (M)$^+$ 574.

b] In analogy to example 4.1., but using in step a] (5Z,7E)—(1S,3R,20R)-1,3-Bis-(tert-butyl-dimethyl-silanyloxy)-20-methyl-9, 10-seco-pregna-5,7,10(19)-trien-1-ol was obtained as colorless foam 1:1 Mixture of (5Z,7E)—(R)— and (S)—N—[(1S,3R,20R)-1,3-dihydroxy-20-methyl-9,10-seco-pregna-5,7,10(19)-trien-21-yl]-4,4,4-trifluoro-3-hydroxy-3-methyl-butyramide

MS: (M+H)$^+$ 500.

NMR (1H, CDCl$_3$, δ, TMS): 0.60 (s, 3H), 0.90 (d, 3H), 1.40 (s; 3H), 1.20–2.07 (m, 15H), 2.31 (m; 2H), 2.41&2.56 (d(AB), 2H), 2.77–3.05 (m; 2H), 3.64 (m, 1H), 4.24 (m, 1H), 4.45 (m, 1H), 45.01 (s br, 1H), 5.34 (s br, 1H), 5.76 (m; N—H), 6.03 (d, 1H), 6.06&6.07 (2s, OH), 6.38 (d, 1H).

EXAMPLE 7

Synthesis of the oxide (E)—(3S,5R)-[2-[3,5-bis-(tert-Butyl-dimethyl-silanyloxy]-2-methylene-cyclohexylidene]-ethyl]-diphenyl-phosphine oxide a) (4R,6S)-4–6-Bis-(tert-butyl-dimethylsilanyloxy)-1-acetoxymethyl-cyclohexene The allylic iodide (4R,6S)-4,6-bis-(tert-butyl-dimethylsilanyloxy)-1-iodomethyl-cyclohexene (J. Org. Chem. 54, 3515–3517 (1989)) (10.55 g; 21,86 mmol) was dissolved in dry N,N-dimethylformamide (50 ml). Cesium acetate (8.65 g; 43 mmol; 2 equivalents) was crushed, azeotropically dried (with toluene) and added to the iodide. After two hours at room temperature the reaction was complete. The reaction mixture was poured onto an aqueous saturated sodium chloride solution and extracted twice with a AcOEt/hexane 1:1 mixture, washed with water, dried over sodium sulfate, and the solvents were removed. Flash chromatography (SiO2, hexane/AcOEt 9/1) afforded 7.76 g (85% yield) of the title compound as a colorless waxy solid.

MS: (M—H)$^+$ 413.

IR: (cm$^{-1}$) 2929; 2846; 2887; 2858; 1746; 1473; 1463; 1377; 1362; 1254; 1235; 1107; 1078; 1062; 1023; 1005; 965; 876; 837; 775.

b) (4R,6S)-4–6-Bis-(tert-butyl-dimethylsilanyloxy)-1-hydroxymethyl-cyclohexene The acetate (4R,6S)-4,6-bis-(tert-butyl-dimethylsilanyloxy)-1-acetoxymethyl-cyclohexene (7.76; 18.71 mmol) was dissolved in dry methanol (60 ml). Potassium carbonate (1.0 g; 7.23 mmol; 0.39 equivalents) was added to the mixture. The reaction was allowed to proceed over night at room temperature. The reaction mixture was poured onto an aqueous solution of 1N HCl and extracted twice with AcOEt, washed with water, dried over sodium sulfate and the solvent was removed. Flash chromatography (SiO2, hexane/AcOEt 8/2) afforded 6.4 g (92%) yield of the title compound as colorless waxy solid.

MS: (M—CH$_2$OH)$^+$ 341; (M—tBu)$^+$ 315.

IR: (cm-1) 3280; 2953; 2928; 2857; 1472; 1461; 1445; 1384; 1360; 1254; 1104; 1080; 1060; 1018; 1002; 988; 933; 877; 838; 775.

c) (4R,6S)-4,6-Bis-(tert-butyl-dimethylsilanyloxy)-1-phenylselenyl-acetoxymethyl-cyclohexene The alcohol (4R,6S)-4,6-bis-(tert-butyl-dimethylsilanyloxy)-1-hydroxymethyl-cyclohexene (1.00 g; 2.68 mmol) was dissolved in dry dichloromethane (15 ml). Phenylselenyl acetic acid (850 mg; 3.49 mmol; 1.3 equivalents), DCC (1100 mg; 5.36 mmol; 2 equivalents), DMAP (165 mg; 1.34 mmol; 0.5 equivalent), were added to the mixture. The reaction was allowed to proceed over night at room temperature. The reaction mixture was poured onto an aqueous saturated sodium chloride solution and extracted twice with a AcOEt/hexane 1:1 mixture, washed with water, dried over sodium sulfate, and the solvents were removed. Flash chromatography (SiO2, hexane/AcOEt 9/1) afforded 1.37 g (89% yield) of the title compound as yellowish oil.

MS: (M—tBu)$^+$ 513.

IR: (cm-1) 2955; 2928; 2886; 2856; 1735; 1668; 1580; 1472; 1257; 1104; 1061; 1000; 875; 837; 775; 737; 692.

d) 2(RS)-[(1RS,3S,5R)-3–5-Bis-(tert-butyl-dimethylsilanyloxy)-2-methylene-cyclohexyl)-1-yl]-2-phenylselenyl-acetic acid methyl ester Mixture of 4 stereoisomers The ester (4R,6S)-4,6-bis-(tert-butyl-dimethylsilanyloxy)-1-phenylselenyl-acetoxymethyl-cyclohexene (610 mg; 1.02 mmol) was dissolved in dry dichloromethane (10 ml) and cooled to 0° C. Triethylamine (0.71 ml; 5.1 mmol; 5 equivalents) was added and the mixture was stirred for 15 minutes. Then t-butyl-dimethyl-silanyl-triflate (tBDMSOTf) (0.544 ml; 2.05 mmol; 2 equivalents) was slowly added. The mixture was allowed to reach room temperature and kept at this temperature over night.

The reaction mixture was poured onto an aqueous solution of 1N HCl and extracted twice with dichloromethane, washed with water, dried over sodium sulfate and the solvent was removed. The crude silyl-ester was dissolved in THF (20 ml); an aqueous solution of 2N NaOH (2 ml; 4 equivalents) was carefully added and allowed to react for half an hour. The reaction mixture was poured onto an aqueous solution of 1N HCl and extracted twice with AcOEt, washed with water, dried over sodium sulfate and the solvents were removed. The crude acid was dissolved in THF (10 ml) and a large excess of an ethereal solution of diazomethane was added carefully untill the reaction was complete (thin layer chromatography control). Then the solvent was removed and flash chromatography (SiO2, hexane/AcOEt 9/1) afforded 595 mg (95% yield) of the title compound as yellowish oil.

NMR: (1H, CDCl3, d, TMS): 7.60 (m. 2H); 7.30 (m; 3H); 5.01 and 4.90 (2s; 1H); 4.70 and 4.68 (2s; 1H); 4.40 (m; 1H); 4.21 (m; 1H); 3.98 and 3.63 (2d; 1H); 3.52 and 3.50 (2s; 3H); 2.94 (m; 1H); 2.25 (m; 1H); 2.00–1.42 (m; 3H); 0.9 (m; 18H); 0.05 (m; 12H).

e) (E)—(1S,5R)-1,5-Bis-(tert-butyl-dimethylsilanyloxy)-2-methylene-3-[ethylidene-2-carboxylic acid methyl ester]-cyclohexane The phenylselenyl-ester 2(RS)-[(1RS,3S,5R)-3–5-bis-(tert-butyl-dimethyl-silanyloxy)-2-methylene-cyclohexyl)-1-yl]-2-phenylselenyl-acetic acid methyl ester (590 mg; 1.00 mmol) was dissolved in THF (10 ml).

A solution of sodium periodate (650 mg; 3 mmol; 3 equivalents) in methanol/water 1:1 mixture (10 ml) was added dropwise. The reaction was allowed to proceed for three hours at room temperature during which time a white precipitate appeared. The reaction mixture was poured onto an aqueous saturated sodium chloride solution and extracted twice with AcOEt, washed with water, dried over sodium sulfate and the solvents were removed. Flash chromatography (SiO2, hexane/AcOEt 95/5) afforded 375 mg (88% yield) of a 1:9 mixture of the title compound and its Z-isomer as colorless waxy solid. This mixture was then dissolved in 100 ml of hexane and irradiated in a photoreactor (Hg lamp). The E/Z isomerization reaction was followed by NMR. After 6 hours the reaction was complete; the solvent was removed and the title compound was obtained in quantitative yield (isomerization step) as colorless waxy solid.

(Z)—(1S,3R)-1,5-Bis-(tert-butyl-dimethylsilanyloxy)-2-methylene-3-[ethylidene-2-carboxylic acid methyl ester]-cyclohexane

MS: (M) 426.

NMR: (1H, CDCl3, d, TMS): 5.62 (s(br); 1H); 5.17 (t; 1H); 4.96 (t; 1H); 4.54 (dd; 1H); 3.63 (s; 3H); 2.42 (dd(AB); 1H); 2.27 (dd(AB); 1H); 1.92 (m; 1H); 1.75 (m; 1H); 0.90 (s; 9H); 0.85 (s; 9H); 0.09 (s; 6H); 0.05 (s; 6H).

(E)—(1S,3R)-1,5-Bis-(tert-butyl-dimethylsilanyloxy)-2-methylene-3-[ethylidene-2-carboxylic acid methyl ester]-cyclohexane

MS: (M) 426.

NMR: (1H, CDCl3, d, TMS): 5.91 (s(br); 1H); 5.07 (t; 2H); 4.58 (dd; 1H); 3.70 (s; 3H); 3.36 (dd(AB); 1H); 2.70 (dd(AB); 1H); 1.84 (m; 1H); 1.76 (m; 1H); 1.32 (m; 3H); 0.89 (s; 9H); 0.85 (s; 9H); 0.07 (s; 6H); 0.06 (s; 6H).

f) (E)—(1S,5R)-1,5-Bis-(tert-butyl-dimethylsilanyloxy)-2-methylene-3-[2-hydroxy-ethylidene]-cyclohexane The ester (E)—(1S,5R)-1,5-bis-(tert-butyl-dimethylsilanyloxy)-2-methylene-3-[ethylidene-2-carboxylic acid methyl ester]-cyclohexane (4.25 g; 9.96 mmol) was dissolved in dry toluene (100 ml) and cooled to −78° C. DIBAL-H (25 ml of a 1.2M solution in toluene; 30 mmol; 3 equivalents) was added dropwise and the mixture was allowed to react for one hour. The reaction was quenched with methanol (3 ml) and warmed to room temperature. Then a 1M aqueous solution of sodium potassium tartrate (30 ml) was added and vigorously stirred till two well layers separated. The organic phase was washed with water, dried over sodium sulfate and the solvent was removed. Flash chromatography (SiO2, hexane/AcOEt 8/2) afforded 2.8 g (70% yield) of the title compound as colorless waxy solid.

MS: (M—OH)$^+$ 381.

IR: (cm$^{-1}$) 3255; 2955; 2928; 2856; 1656; 1638; 1472; 1463; 1443; 1407; 1361; 1255; 1130; 1105; 1080; 1047; 1029; 1008; 987; 907; 897; 836; 775.

g) (E)—(1S,5R)-1,5-Bis-(tert-butyl-dimethylsilanyloxy)-2-methylene-3-[2-chloro-ethylidene]-cyclohexane N-chlorosuccinimide (NCS) (1.92 g; 14.35 mmol; 2 equivalents) was dissolved in dry dichloromethane (50 ml) and cooled to 0° C.; then dimethylsulfide (1.10 ml; 14.35 mmol; 2 equivalents) was added and the mixture was stirred for a quarter of an hour (formation of a white precipitate) and then cooled to −20° C. The allylic alcohol (E)—(1S,5R)-1,5-bis-(tert-butyl-dimethylsilanyloxy)-2-methylene-3-[2-hydroxy-ethylidene]-cyclohexane (2.8 g; 7.02 mmol), dissolved in dry dichloromethane (20 ml), was added dropwise. The mixture was allowed to react for half an hour at −20° C. and then the temperature was allowed to reach room temperature. The reaction mixture was poured onto an aqueous saturated sodium chloride solution and extracted twice with ether, washed with water, dried over sodium sulfate and the solvents were removed. Flash chromatography (SiO2, hexane/AcOEt 95/5) afforded 2.82 g (96% yield) of the title compound as yellowish oil.

MS: (M—Cl)$^+$ 381.

IR: (cm$^{-1}$) 2955; 2928; 2886; 2858; 1652; 1472; 1463; 1256; 1124; 1104; 1080; 902; 836; 776.

h) (E)—(3S,5R]-[2-[3,5-Bis-tert-butyl-dimethylsilanyloxy]-2-methylene-cyclohexylidene]-ethyl] diphenylphosphine oxide Diphenylphosphine (2.37 ml; 13.5 mmol; 2 equivalents) was dissolved in dry THF (40 ml) and cooled to 0° C.; then butyllithium (8.65 ml of a 1.6M sol. in hexane; 13.5 mmol; 2 equivalents) was added dropwise and the mixture was stirred for a quarter of an hour. A deep red solution was obtained.

The allylic chloride (E)—(1S,5R)-1,5-bis-(tert-butyl-dimethylsilanyloxy)-2-methylene-3-[2-chloro-ethylidene]-cyclohexane (2.82 g; 6.76 mmol), dissolved in dry THF (20 ml), was cooled to −78° C. and the above prepared lithium diphenylphosphide was added dropwise till the reaction mixture took an orange color. The reaction was quenched with methanol (1 ml), and then the temperature was allowed to reach room temperature.

The solvent was removed, the reaction mixture was taken up in AcOEt (30 ml), cooled to 0° C., and a 10% H$_2$O$_2$ solution (30 ml) was added carefully, and the mixture was stirred for a quarter of an hour. The organic layer was washed with water, dried over sodium sulfate and the solvent was removed. Flash chromatography (SiO2, dichloromethane/AcOEt 8/2) afforded 2.86 g (72% yield) of the title compound as colorless waxy solid.

MS: (M)$^+$ 582.

IR: (cm$^{-1}$) 3425; 3270; 2954; 2928; 2886; 2856; 1630; 1472; 1438; 1253; 1211; 1189; 1121; 1082; 1023; 1004; 903; 837; 776; 745; 720; 695.

What is claimed is:

1. A compound of the formula I

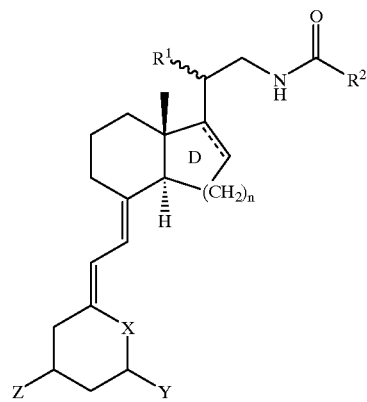

wherein
X is C=CH$_2$ or CH$_2$;
Y is hydrogen, fluorine or hydroxy
Z is hydroxy
n is 1 or 2
R$^1$ is lower alkyl,
R$^2$ is a branched alkyl having 3 to 8 carbon atoms which is unsubstituted or substituted with one or more halogen or OH substituents, or is a phenyl group which is unsubstituted or substituted with a branched alkyl having 3 to 8 carbon atoms which is unsubstituted or substituted with one or more halogen or OH substituents;
and the dotted carbon-carbon bond in ring D is —C—C— or —C=C—; or a pharmaceutically usable salt thereof.

2. A compound according to claim 1, wherein Y is hydrogen or hydroxy.

3. A compound according to claim 2, wherein Y is hydroxy.

4. A compound according to claim 3, wherein n is 2.

5. A compound according to claim 4, wherein the dotted carbon—carbon bond in ring D is —C—C—.

6. A compound according to claim 5, wherein R$^2$ is a branched alkyl having 3 to 8 carbon atoms which is unsubstituted or substituted with one or more halogen or OH substituents.

7. A compound according to claim 6, wherein $R^2$ is 2-hydroxy-2-methylpropyl, 2-hydroxy-2-trifluoromethylpropyl and 3,3,3-trifluoro-2-hydroxy-2-trifluoromethylpropyl.

8. A compound according to claim 6, wherein the compound is (E)—(R)—N—[(1R,3R,20S)-1,3-Dihydroxy-17a,20a-dihomo-19-nor-9,10-seco-pregna-5,7-dien-21-yl]-4,4,4-trifluoro-3-hydroxy-3-methyl-butyramide.

9. A compound according to claim 6, wherein the compound is (E)—(S)—N—[(1R,3R,20S)-1,3-Dihydroxy-17a,20a-dihomo-19-nor-9,10-seco-pregna-5,7-dien-21-yl]-4,4,4-trifluoro-3-hydroxy-3-methyl-butyramide.

10. A compound according to claim 6, wherein the compound is (E)—N—[(1R,3R,20S)-1,3-Dihydroxy-17a,20a-dihomo-19-nor-9,10-seco-pregna-5,7-dien-21-yl]-4,4,4-trifluoro-3-trifluoromethyl-3-hydroxy-butyramide.

11. A compound according to claim 4, wherein the dotted carbon—carbon bond in ring D is —C=C—.

12. A compound according to claim 11, wherein $R^2$ is a branched alkyl having 3 to 8 carbon atoms which is unsubstituted or substituted with one or more halogen or OH substituents.

13. A compound according to claim 11, wherein $R^2$ is 2-hydroxy-2-methylpropyl, 2-hydroxy-2-trifluoromethylpropyl and 3,3,3-trifluoro-2-hydroxy-2-trifluoromethylpropyl.

14. A compound according to claim 2, wherein n is 1 and the dotted carbon—carbon double bond in ring D is —C—C—.

15. A compound according to claim 14, wherein $R^2$ is a branched alkyl having 3 to 8 carbon atoms which is unsubstituted or substituted with one or more halogen or OH substituents.

16. A compound according to claim 15, wherein $R^2$ is 2-hydroxy-2-methylpropyl, 2-hydroxy-2-trifluoromethylpropyl and 3,3,3-trifluoro-2-hydroxy-2-trifluoromethylpropyl.

17. A compound according to claim 15, wherein the compound is (E)—(1R,3R,20S)—N-(1,3-Dihydroxy-20-methyl-19-nor-9,10-seco-pregna-5,7-dien-21-yl)-4,4,4-trifluoro-3-hydroxy-3-trifluoromethyl-butyramide.

18. A compound according to claim 14, wherein the compound is (E)—(1R,3R,20S)—N-(1,3-Dihydroxy-20-methyl-19-nor-9,10-seco-pregna-5,7-dien-21-yl)-3-(1-hydroxy-1-methyl-ethyl)-benzamide.

19. A compound according to claim 15, wherein the compound is (E)—(1R,3R,20S)—N-(1,3-Dihydroxy-20-methyl-19-nor-9,10-seco-pregna-5,7-dien-21-yl)-2,2-dimethyl-propionamide.

20. A compound according to claim 15, wherein the compound is (E)—(1R,3R,20S)—N-(1,3-Dihydroxy-20-methyl-19-nor-9,10-seco-pregna-5,7-dien-21-yl)-2-hydroxy-2-methyl-propionamide.

21. A compound according to claim 15, wherein the compound is E—(R)—N—[(1R,3R,20S)-1,3-dihydroxy-20-methyl-19-nor-9,10-seco-pregna-5,7-dien-21-yl]-4,4,4-trifluoro-3-hydroxy-3-methyl-butyramide.

22. A composition comprising a 1:1 mixture of (R) and (S) stereoisomers of a compound of the formula I

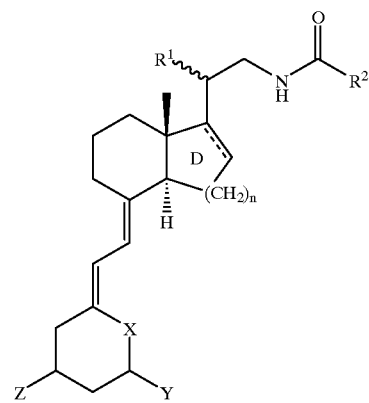

wherein

X is C=CH 2 or CH2;

Y is hydrogen, fluorine or hydroxy

Z is hydroxy n is 1 or 2

R1 is lower alkyl,

R2 is a branched alkyl having 3 to 8 carbon atoms which is unsubstituted or substituted with one or more halogen or OH substituents, or is a phenyl group which is unsubstituted or substituted with a branched alkyl having 3 to 8 carbon atoms which is unsubstituted or substituted with one or more halogen or OH substituents;

and the dotted carbon—carbon bond in ring D is —C—C— or —C=C—; or a pharmaceutically usable salt thereof.

23. A composition according to claim 22, wherein Y is hydrogen or hydroxy.

24. A composition according to claim 22, wherein n is 1 and the dotted carbon—carbon double bond is —C—C—.

25. A composition according to claim 23, wherein $R^2$ is a branched alkyl having 3 to 8 carbon atoms which is unsubstituted or substituted with one or more halogen or OH substituents.

26. A composition according to claim 24, wherein the mixture is a 1:1 mixture of[5E,7E)—(R) and —(S)-4,4,4-trifluoro-3-hydroxy-N—[(1S,3R,20S)-1,3-dihydroxy-20-methyl-9,10-seco-pregna-5,7,10(19)-trien-21-yl]-3-methyl-butyramide.

27. A composition according to claim 24, wherein the mixture is a 1:1 mixture of [E]—(R) and —(S)—N—[(1R,3R,20S)-1,3-dihydroxy-20-methyl-19-nor-9,10-seco-pregna-5,7-dien-21yl]-4,4,4-trifluoro-3-hydroxy-3-methyl-butyramide.

28. A composition according to claim 24, wherein the mixture is a 1:1 mixture of (5Z,7E)—(R)— and —(S)—N—[(3S,20S)-3-hydroxy-20-methyl-9,10-seco-pregna-5,7,10(19)-trien-21-yl]4,4,4-trifluoro-3-hydroxy-3-methyl-butyramide.

29. A composition according to claim 22, wherein n is 2 and the dotted carbon—carbon bond in ring D is —C=C—.

30. A composition according to claim 29, wherein $R^2$ is a branched alkyl having 3 to 8 carbon atoms which is unsubstituted or substituted with one or more halogen or OH substituents.

31. A composition according to claim 24, wherein the mixture is a 1:1 mixture of (5Z,7E)—(R)— and (S)—N—[(1S,3R,20S)-1,3-dihydroxy-17a,20a -dihomo-9,10-seco-pregna-5,7,10(19),17-tetraen-21-yl]-4,4,4-trifluoro-3-hydroxy-3-methyl-butyramide.

32. A composition according to claim 30, wherein the mixture is a 1:1 mixture of(E)—(R)— and (S)—N—(1R, 3R,20S)-1,3-dihydroxy-17a,20a-dihomo-19-nor-9,10-seco-pregna-(5,7,7-trien-21-yl)-4,4,4-trifluoro-3-hydroxy-3-methyl-butyramide.

33. A composition according to claim 25, wherein the mixture is a 1:1 mixture of (5Z,7E)—(R)— and (S)—N—[(1S,3R,20S)-1,3-dihydroxy-20-methyl-9,10-seco-pregna-5,7,10(19)-trien-21-yl]-4,4,4-trifluoro-3-hydroxy-3-methyl-butyramide.

34. A composition according to claim 25, wherein the mixture is a 1:1 mixture of (E)—(R)— and (S)—N—(1R, 3R,20S)-1,3-dihydroxy-20-methyl-19-nor-9,10-seco-pregna-5,7-dien-21-yl]-4,4,4-trifluoro-3-hydroxy-3-methyl-butyramide.

35. A composition according to claim 25, wherein the mixture is a 1:1 mixture of (E)—(S)— and (R)—N—(1R, 3R,20R)-1,3-dihydroxy-20-methyl-19-nor-9,10-seco-pregna-5,7-dien-21-yl]-4,4,4-trifluoro-3-hydroxy-3-methyl-butyramide.

36. A composition according to claim 25, wherein the mixture is a 1:1 mixture of (5Z,7E)—(R)— and (S)—N—[(3S,20R)-3-hydroxy-20-methyl-9,10-seco-pregna-5,7,10(19)-trien-21-yl]-4,4,4-trifluoro-3-hydroxy-3-methyl-butyramide.

37. A composition according to claim 25, wherein the mixture is a 1:1 mixture of (5Z,7E)—(R)— and (S)—N—[(1S,3R,20R)-1,3-dihydroxy-20-methyl-9,10-seco-pregna-5,7,10(19)-trien-21-yl]-4,4,4-trifluoro-3-hydroxy-3-methyl-butyramide.

* * * * *